(12) United States Patent
Cheng et al.

(10) Patent No.: US 10,058,620 B2
(45) Date of Patent: Aug. 28, 2018

(54) DEXTRAN-PEPTIDE HYBRID FOR EFFICIENT GENE DELIVERY

(71) Applicants: Gang Cheng, Fairlawn, OH (US); Qiong Tang, Breckville, OH (US); Bin Cao, Allison Park, PA (US)

(72) Inventors: Gang Cheng, Fairlawn, OH (US); Qiong Tang, Breckville, OH (US); Bin Cao, Allison Park, PA (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 14/621,904

(22) Filed: Feb. 13, 2015

(65) Prior Publication Data

US 2015/0231274 A1    Aug. 20, 2015

Related U.S. Application Data

(60) Provisional application No. 61/939,951, filed on Feb. 14, 2014.

(51) Int. Cl.
| | | |
|---|---|---|
| *A61K 47/48* | (2006.01) | |
| *A61K 48/00* | (2006.01) | |
| *C12N 15/87* | (2006.01) | |
| *A61K 47/61* | (2017.01) | |
| *A61K 47/64* | (2017.01) | |

(52) U.S. Cl.
CPC ........ *A61K 47/48315* (2013.01); *A61K 47/61* (2017.08); *A61K 47/645* (2017.08); *C12N 15/87* (2013.01); *C12N 2810/40* (2013.01)

(58) Field of Classification Search
CPC .......... A61K 47/48315; A61K 48/0041; A61K 47/61; A61K 47/645; C12N 15/87; C12N 2810/40
USPC ....................................................... 530/322
See application file for complete search history.

(56) References Cited

U.S. PATENT DOCUMENTS 3,912,662 A * 10/1975 Martinsson .............. C11D 1/94
510/340
2011/0305898 A1* 12/2011 Zhang ..................... A61L 27/34
428/336

OTHER PUBLICATIONS

Tang et al. Cholesterol-Peptide Hybrids to Form Liposome-Like Vesicles for Gene Delivery. PLoS ONE 8(1): e54460, Jan. 30, 2013.*
Kim et al. Synthesis and characterization of dextran—methacrylate hydrogels and structural study by SEM. J Biomed Mater Res, 49, 517-527, 2000.*
Toncheva et al. Novel vectors for gene delivery formed by self-assembly of DNA with poly(L-lysine) grafted with hydrophilic polymers. Biochimica et Biophysica Acta 1380 (1998) 354-368. (Year: 1998).*
Yudovin-Farber, I. and Domb, A.J., "Cationic polysaccharides for gene delivery" Material Science and Engineering C 27 (2007) 595-598.
Martin, M.: Rice, K., "Peptide-guided gene delivery." The AAPS Journal 2007, 9, (1), E18-E29.
Jiang, D. H.; Salem. A. K., "Optimized dextran-polyethylenimine conjugates are efficient non-viral vectors with reduced cytotoxicity when used in serum containing environments." International Journal of Pharmaceutics 2012, 427, (1), 71-79.

* cited by examiner

*Primary Examiner* — Yih-Horng Shiao
(74) *Attorney, Agent, or Firm* — Renner Kenner Greive Bobak Taylor & Weber

(57) ABSTRACT

One or more embodiments of the present invention provide a novel composition for gene delivery are directed to a group of polysaccharide polymers, having one or more nucleic acid delivery side chains comprising cationic peptides. In some embodiments, these cationic peptides condense and physically bond to one or more nucleic acids to form a polysaccharide-nucleic acid complex that permits delivery to and transfection of the nucleic acid(s) into cells. In some embodiments, the polysaccharide polymers of the present invention may also have one or more zwitterionic side chains and/or reactive side chains.

18 Claims, 10 Drawing Sheets

Specification includes a Sequence Listing.

SEQUENCE LISTING

<160> NUMBER OF SEQ ID NOS: 7

<210> SEQ ID NO 1
<211> LENGTH: 11
<212> TYPE: PRT
<213> ORGANISM: Artificial Sequence
<220> FEATURE:
<223> OTHER INFORMATION: Artificially generated oligomer.

<400> SEQUENCE: 1

Cys His His His His His Arg Arg Arg Arg Arg
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Artificially generated oligomer sequence.

<400> SEQUENCE: 2

Cys Arg Arg Arg Arg Arg His His His His His
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Artificially generated oligomer.

<400> SEQUENCE: 3

Cys Lys Lys Lys Lys Lys His His His His His
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Artificially generated oligomer.

<400> SEQUENCE: 4

Cys His His His His His Lys Lys Lys Lys Lys
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Artificially generated oligomer.

<400> SEQUENCE: 5

Arg Arg Arg Arg Arg His His His His His Cys
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Artificially generated oligomer.

<400> SEQUENCE: 6

Lys Lys Lys Lys Lys His His His His His Cys
1               5                   10

```
<210> SEQ ID NO 7
<211> LENGTH: 10
<212> TYPE: PRT
<213> ORGANISM: Artificial Sequence
<220> FEATURE:
<223> OTHER INFORMATION: Artificially generated oligomer.

<400> SEQUENCE: 7

Arg Arg Arg Arg Arg His His His His His
1               5                   10
```

DEXTRAN-PEPTIDE HYBRID FOR EFFICIENT GENE DELIVERY

CROSS REFERENCE TO RELATED APPLICATIONS

This application claims the benefit of U.S. provisional patent application Ser. No. 61/939,951 entitled "Dextran-Peptide Hybrid for Efficient Gene Delivery," filed Feb. 14, 2014, and incorporated herein by reference in its entirety.

REFERENCE TO GOVERNMENT SUPPORT

This invention was made with government support under DMR-1206923 awarded by the National Science Foundation (NSF). The United States government has certain rights in the invention.

FIELD OF THE INVENTION

One or more embodiments of the present invention relates to a novel composition for gene delivery. In certain embodiments, the present invention is directed to polysaccharide polymers having one or more side chains comprising cationic peptides that can complex and deliver nucleic acids to cells.

SEQUENCE LISTING

The Sequence Listing file UOA.1111.US Sequence Listing_ST25.txt having a size of 1,759 bytes and creation date of Jan. 21, 2015, that was electronically filed with the present application is incorporated herein by reference in its entirety.

BACKGROUND OF THE INVENTION

Gene therapy has drawn significant interest in the past two decades, since it is a promising strategy for the treatment of genetic disorders or acquired diseases that are currently considered incurable. The success of gene therapy relies on safe and efficient gene delivery systems. These systems must have following characteristics, DNA protection, cellular uptake, endosomal escape and low toxicity, to overcome obstacles in gene therapy. So far, various delivery systems have been developed, and they can be grouped into two categories: viral and non-viral vectors. Non-viral vectors are not as efficient as viral vectors, but provide safer delivery strategies since they could avoid the problems associated with viruses, including complexity of production, immunogenicity and mutagenesis. Currently, the majority of non-viral vectors are made of synthetic materials, such as cationic lipids, polymers, and dendrimers. Some of them could induce high gene transfection in vitro; however, many of these systems had high toxicity, low biodegradability and poor biocompatibility in vivo.

Natural materials, such as cationic polysaccharides and peptides, have been studied as potential gene delivery carriers to avoid the chronic toxicity associated with carriers based on synthetic materials. Chitosan has been intensively studied as the gene delivery carrier due to its biocompatibility, but its transfection efficiency is still unsatisfactory and the solubility at neutral condition is low. Peptide vectors, composed of natural amino acids, are compatible with biological environment, less cytotoxic and biodegradable. In addition, these vectors are adaptable to rational design since amino acid building blocks with diverse properties provide us the freedom for developing multifunctional drug carriers with the desired functions. For example, arginine residue which is positively charged in physiological environment has been used to condense negatively charged therapeutic DNA or RNA. Histidine residue is introduced into peptides to help DNA escape from endosome and thus to improve transfection efficiency. A previous study demonstrated that integrated peptides with ligand peptide sequence can achieve targeted gene delivery to the specific cells. However, the size of the peptide has to be over a certain value to accommodate all desired functions and it will dramatically increase the cost of the peptide.

In general, there have been three major obstacles for the further development of natural polymer-based gene carriers. Firstly, all of the reported gene drug vectors have provided only part of required functions, such as high transfection efficiency, long blood circulation and effective targeting properties. Secondly, the gene transfection efficiency of natural polymer in general has been low. Thirdly, drug loading efficiency of these natural polymer based carriers has also been low and thus optimal gene transfection is achieved at relatively high N/P ratios. What is needed in the art is a gene delivery system that uses a biodegradable, efficient and integrated natural polymer and has high transfection efficiency, long blood circulation and effective targeting properties.

SUMMARY OF THE INVENTION

One or more embodiments of the present invention provide a novel composition for gene delivery are directed to a group of polysaccharide polymers, having one or more nucleic acid delivery side chains comprising cationic peptides. In some embodiments, these cationic peptides condense and physically bond to one or more nucleic acids to form a polysaccharide-nucleic acid complex that permits delivery to and transfection of the nucleic acid(s) into cells. In some embodiments, the polysaccharide polymers of the present invention may also have one or more zwitterionic side chains and/or reactive side chains.

In a first aspect, the present invention is directed to a polysaccharide polymer composition for nucleic acid delivery comprising: a polysaccharide polymer chain and one or more nucleic acid delivery side chains bonded to said polysaccharide polymer chain, wherein said one or more nucleic acid delivery side chains further comprise a cationic peptide. In one or more embodiments of the first aspect of the present invention polysaccharide polymer composition further comprises one or more nucleic acids physically bonded to said cationic peptide to form a polysaccharide-nucleic acid complex.

In one or more embodiments, the polysaccharide polymer composition may include any one or more of the above referenced embodiments of the first aspect of the present invention wherein said polysaccharide polymer chain comprises dextran, cellulose, starch, glycosaminoglycans, mannan, dextrin, agar, agarose, alginic acid, alguronic acid, amylose, alpha glucan, amylopectin, beta-glucan, callose, carrageenan, cellodextrin, chitin, chitosan, chrysolaminarin, cyclodextrin, DEAE-sepharose, ficoll, fructan, fucoidan, galactoglucomannan, galactomannan, gellan gum, glucan, glucomannan, glucuronoxylan, glycocalyx, glycogen, hemicellulose, homopolysaccharide, hypromellose, inulin, laminarin, lentinan, levan polysaccharide, lichenin, mixed-linkage glucan, paramylon, pectic acid, pectin, pentastarch, phytoglycogen, pleuran, polydextrose, polysaccharide peptide, porphyran, pullulan, sepharose, xylan, xyloglucan, zymosan, hyaluronan, heparin or combinations thereof. In one or more embodiments, the polysaccharide polymer composition may include any one or more of the above referenced embodiments of the first aspect of the present invention wherein said polysaccharide polymer chain has a weight average molecular weight of from about 500 daltons to about 1,000,000 daltons.

In one or more embodiments, the polysaccharide polymer composition may include any one or more of the above referenced embodiments of the first aspect of the present invention wherein said one or more nucleic acid delivery side chains further comprise methacrylate, acrylate, methacrylate, methacrylamide, acrylamide, maleimide, haloacetyl, and pyridyl disulfide, thiol or combinations thereof.

In one or more embodiments, the polysaccharide polymer composition may include any one or more of the above referenced embodiments of the first aspect of the present invention wherein the cationic peptide on each of said one or more nucleic acid delivery side chains is a random copolymer having a formula selected from the group consisting of $C_wR_5$, $C_wR_3H_3$, $C_wK_5$, $C_wK_3$, $C_wR_5H_5$, $C_wR_3H_3$, $C_wK_5H_5$, $C_wK_3H_3$, $C_wR_m$, $C_wK_n$, $C_wR_oH_p$, $C_wK_pH_q$, or $C_wR_xK_yH_z$; wherein C is cysteine, R is arginine, K is lysine, H is histidine, and m, n, o, p, q, x, y, z and w are integers from 1 to 1,000. In one or more embodiments, the polysaccharide polymer composition may include any one or more of the above referenced embodiments of the first aspect of the present invention wherein the cationic peptide on each of said one or more nucleic acid delivery side chains is a block copolymer having a formula selected from the group consisting of $CR_5$, $CR_3H_3$, $CH_3R_3$, $CK_5$, $CK_3$, $CH_5R_5$ (SEQ. ID No. 1), $CR_5H_5$ (SEQ. ID No. 2), $CR_3H_3$, $CH_3R_3$, $CK_5H_5$ (SEQ. ID No. 3), $CH_5K_5$ (SEQ. ID No. 4), $CK_3H_3$, $CH_3K_3$, $R_5C$, $R_3H_3C$, $K_5C$, $K_3C$, $R_5H_5C$ (SEQ. ID No. 5), $R_3H_3C$, $K_5H_5C$ (SEQ. ID No. 6), $K_3H_3C$, $CR_m$, $CK_n$, $CR_oH_p$, $CK_pH_q$, or $CR_xK_yH_z$; wherein C is cysteine, R is arginine, K is lysine, H is histidine, and m, n, o, p, q, x, y, z and w are integers from 1 to 1,000.

In one or more embodiments, the polysaccharide polymer composition may include any one or more of the above referenced embodiments of the first aspect of the present invention wherein said—cationic peptide comprises from about 1 to about 10000 arginine residues, from about 1 to about 10000 histidine residues and at least one cysteine residue. In one or more embodiments, the polysaccharide polymer composition may include any one or more of the above referenced embodiments of the first aspect of the present invention wherein said cationic peptide comprises from about 1 to about 10000 lysine residues, from about 1 to about 10000 histidine residues and at least one cysteine residue. In one or more embodiments, the polysaccharide polymer composition may include any one or more of the above referenced embodiments of the first aspect of the present invention wherein said cationic peptide has the formula $NH_2$—RRRRRHHHHHC—COOH (SEQ. ID No. 5).

In one or more embodiments, the polysaccharide polymer composition may include any one or more of the above referenced embodiments of the first aspect of the present invention wherein said one or more nucleic acid delivery side chains further comprise a linker molecule bound to said polysaccharide polymer chain; wherein said cationic peptide is bonded to said linker molecule by a thiol bond.

In one or more embodiments, the polysaccharide polymer composition may include any one or more of the above referenced embodiments of the first aspect of the present invention wherein the polysaccharide-nucleic acid complex has an N to P ratio of from about 1:1 to about 100:1. In one or more embodiments, the polysaccharide polymer composition may include any one or more of the above referenced embodiments of the first aspect of the present invention wherein the polysaccharide-nucleic acid complex has an N to P ratio of from about 1:1 to about 10:1.

In one or more embodiments, the polysaccharide polymer composition may include any one or more of the above referenced embodiments of the first aspect of the present invention wherein said one or more nucleic acids comprise ribonucleic acids, deoxyribonucleic acids or combinations thereof. In one or more embodiments, the polysaccharide polymer composition may include any one or more of the above referenced embodiments of the first aspect of the present invention wherein said one or more nucleic acids are selected from the group consisting of Plasmid DNA, Oligonucleotides, Aptamers, DNAzymes, RNA Aptamers, RNA Decoys, Antisense RNA, Ribozymes, small interfering RNA (siRNA), microRNA (miRNA), short hairpin RNA, Antagomirs, and combinations thereof.

In a second aspect, the present invention is directed to any one or more of the polysaccharide polymer compositions of the first aspect described above, further comprising one or more zwitterionic side chains. In one or more embodiments, the polysaccharide polymer composition may include any one or more of the above referenced embodiments of the second aspect of the present invention wherein said one or more zwitterionic side chains further comprise a zwitterionic moiety, said zwitterionic moiety comprising a carboxybetaine group, a sulfobetaine group, a phosphobetaine group or any combinations thereof. In one or more embodiments, the polysaccharide polymer composition may include any one or more of the above referenced embodiments of the second aspect of the present invention, wherein said zwitterionic moiety has a corresponding cationic ring form.

In a third aspect, the present invention is directed to any one or more of the polysaccharide polymer compositions of the first and second aspects described above, further comprising one or more reactive side chains comprising a compound selected from the group consisting of acrylates, methacrylates, methacrylamides, acrylamides, maleimides, haloacetyls, pyridyl disulfides, thiols and combinations thereof.

BRIEF DESCRIPTION OF THE DRAWINGS

For a more complete understanding of the features and advantages of the present invention, reference is now made to the detailed description of the invention along with the accompanying figures in which.

Figures 6A, 6B, 6C, 6D, 6E:
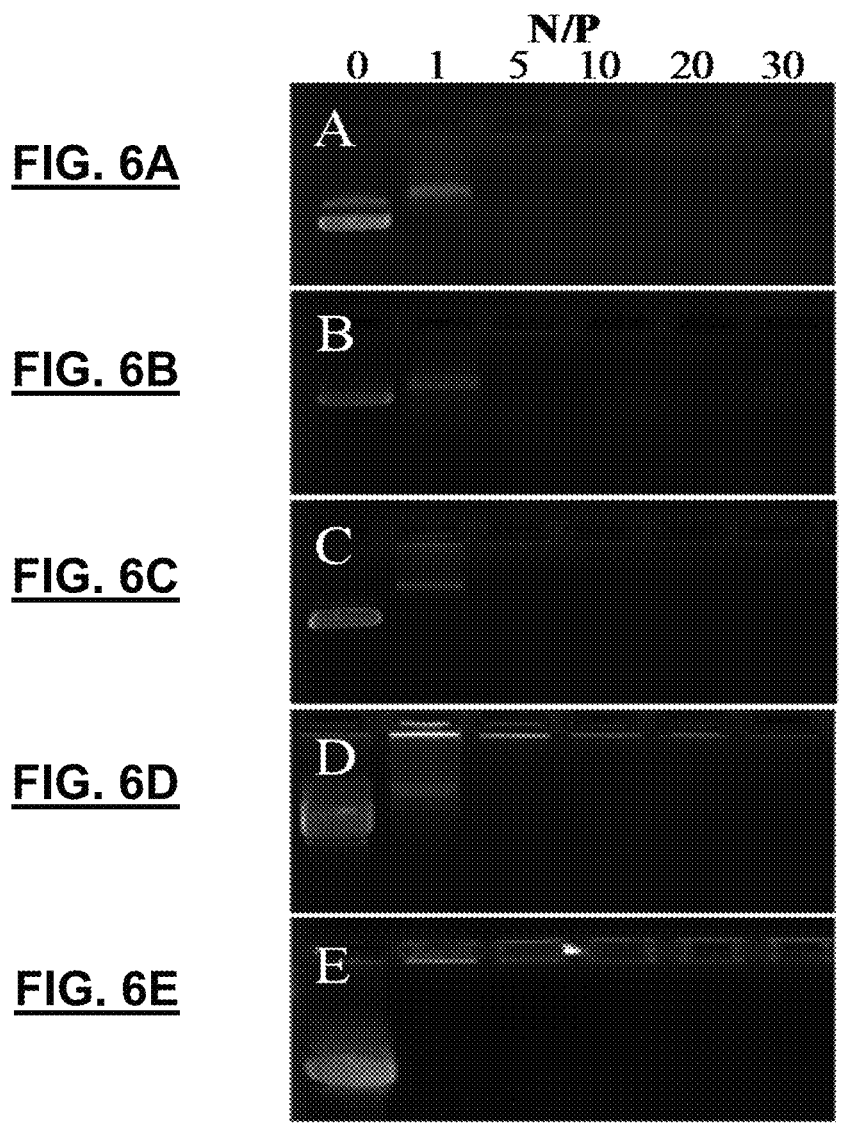
FIGS. 6A-E are images showing the results of electrophoretic mobility assays of DNA in Dex10-$R_5H_5$ (20%)/

DNA (FIG. 6A), Dex10-R$_5$H$_5$ (40%)/DNA (FIG. 6B), Dex20-R$_5$H$_5$ (10%)/DNA (FIG. 6C), Dex20-R$_5$H$_5$ (20%)/DNA (FIG. 6D) and Dex70-R$_5$H$_5$ (10%)/DNA (FIG. 6E) complexes at N/P ratios of 0, 1, 5, 10, 20 and 30, respectively.

Figure 7A:
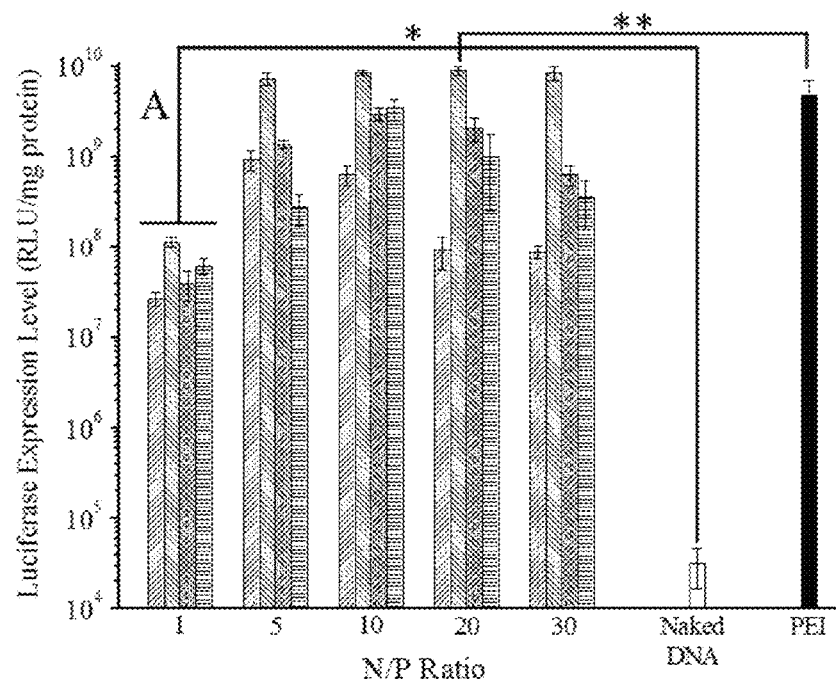
Figure 7B:
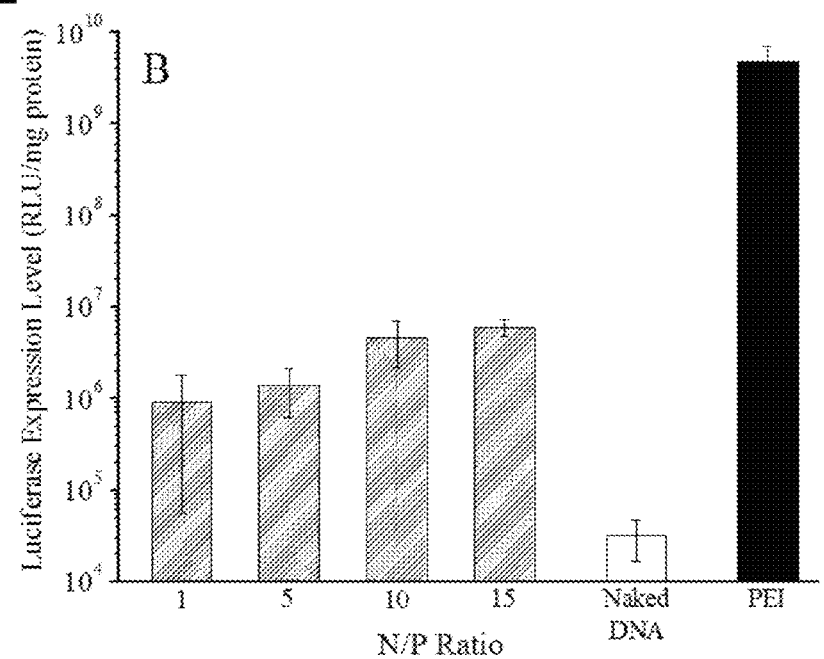

FIGS. 7A-B are graphs showing luciferase expression levels induced by (FIG. 7A) Dex10-R$_5$H$_5$ (20%)/DNA (▨), Dex10-R$_5$H$_5$ (40%)/DNA (▧), Dex20-R5H5(10%)/DNA (▨), and Dex20-R$_5$H$_5$ (20%)/DNA (▤) and (FIG. 7B) Dex70-R$_5$H$_5$/DNA in SKOV3 cell line. DNA and PEI-DNA complex at an N/P ratio of 5 are used as negative and positive controls respectively. Error bars represent standard deviation of 4 replicates. *, ** P<0.05.

Figure 8A:
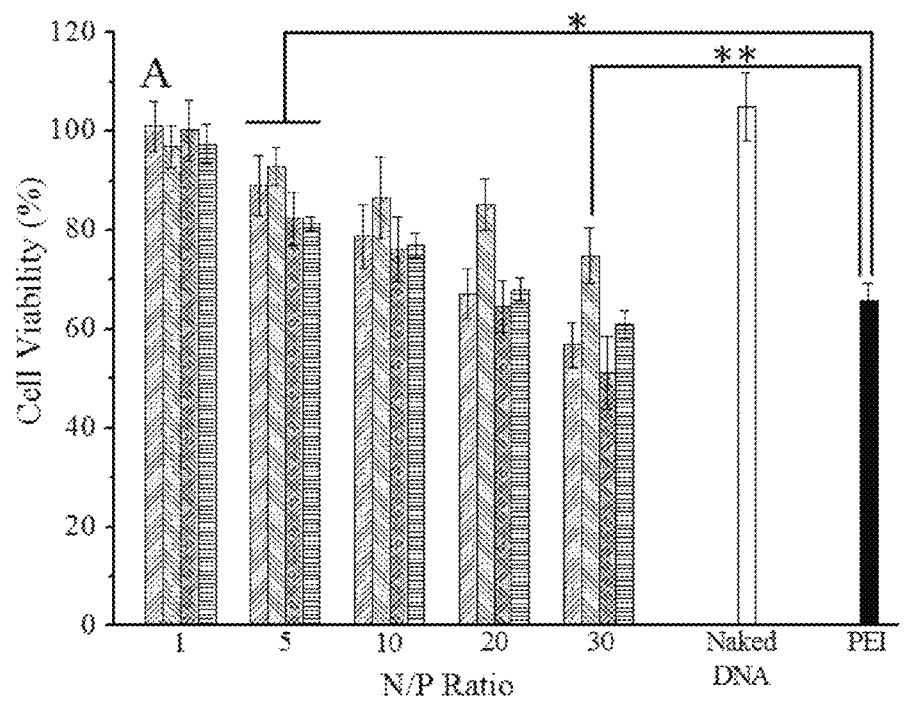
Figure 8B:
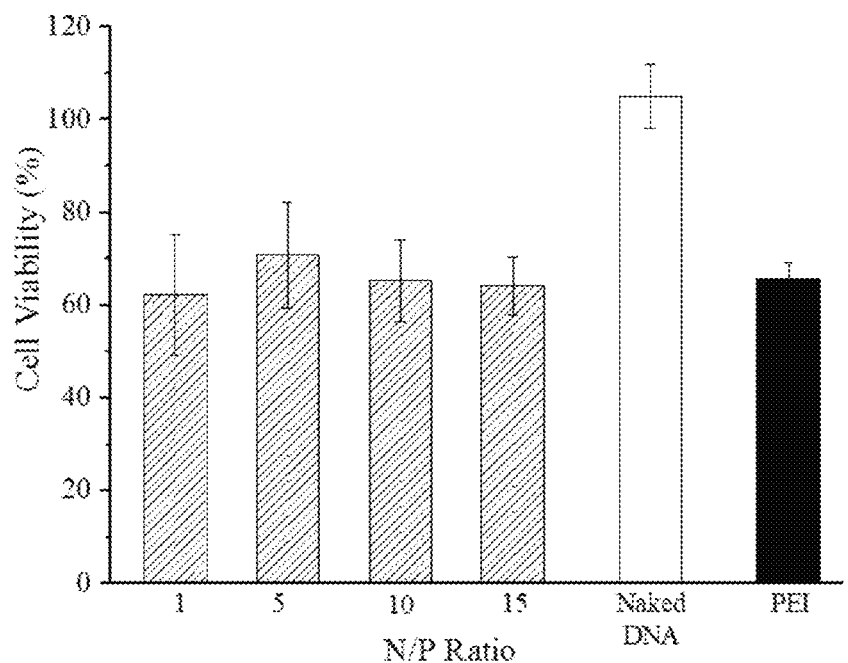

FIGS. 8A-B are graphs showing cell viability of SKOV3 cell line after incubation with (FIG. 8A) Dex10-R$_5$H$_5$ (20%)/DNA (▨), Dex10-R$_5$H$_5$ (40%)/DNA (▧), Dex20-R$_5$H$_5$ (10%)/DNA (▨) and Dex20-R$_5$H$_5$ (20%)/DNA (▤) complexes and (FIG. 8B) Dex70-R$_5$H$_5$/DNA at different N/P ratios compared to DNA and PEI-DNA complex at an N/P ratio of 5. The DNA concentration is 5 μg/mL. Error bars represent standard deviation of 8 replicates. *, ** P<0.05

Figure 9:
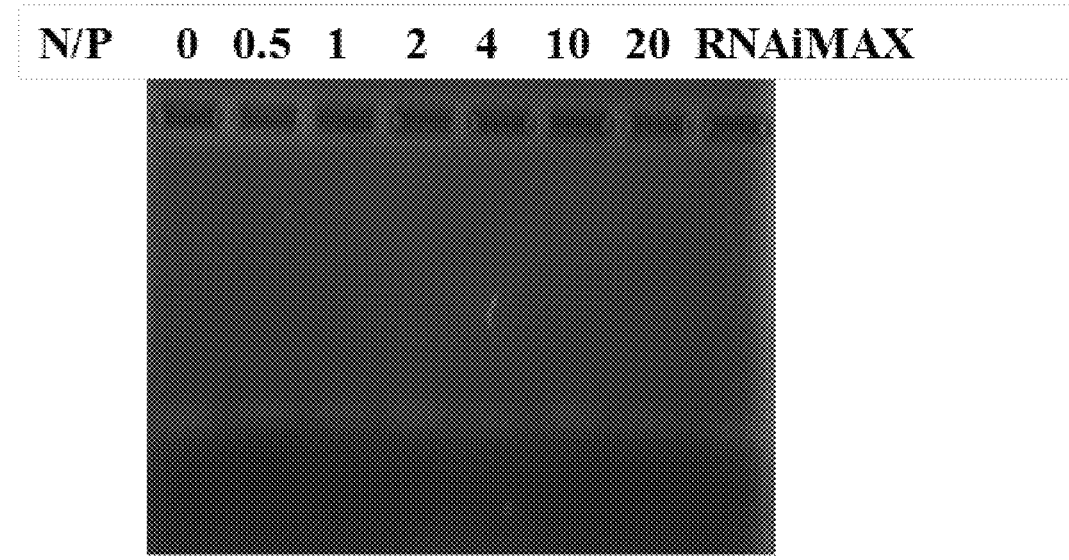

FIG. 9 is an image showing the results of electrophoretic mobility assays of miRNA antagomir complexed with Dex10-R$_5$H$_5$ (40%) at different N/P ratios and RNAiMAX at a designed ratio following its protocol.

Figure 10:
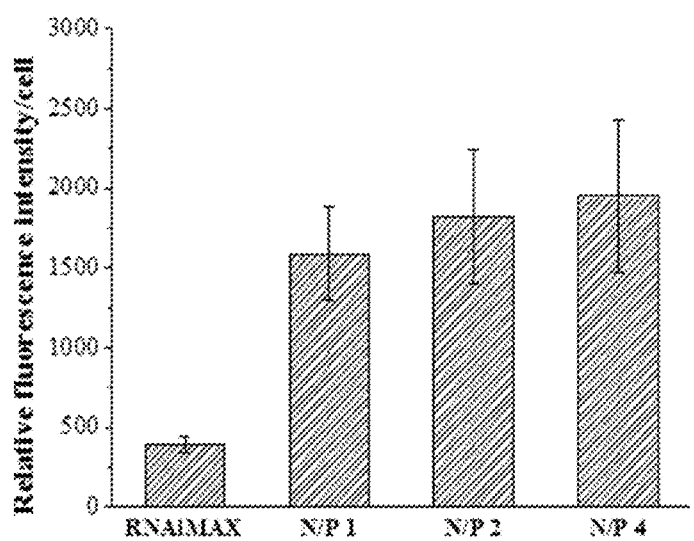

FIG. 10 is a graph showing the results of intracellular localization assays of Dex-R$_5$H$_5$/microRNA complexes in HepG2 cells showing cellular internalization of formulations of Dex10k-R$_5$H$_5$ (40%)/miRNA149 inhibitor complexes at N/P ratios of 1, 2, and 4, and of RNAiMAX/miRNA149 antagomir complexes at the designed ratio following the RNAiMAX protocol after 6-hour incubation. The miRNA was stained by TM-Rhodamine (red) and cell nuclei were stained by Hoechst 33342 (blue). The measured fluorescence intensity of each sample presented as total red fluorescence value/cell. Error bars represent standard deviation of 4 replicates.

Figure 11:
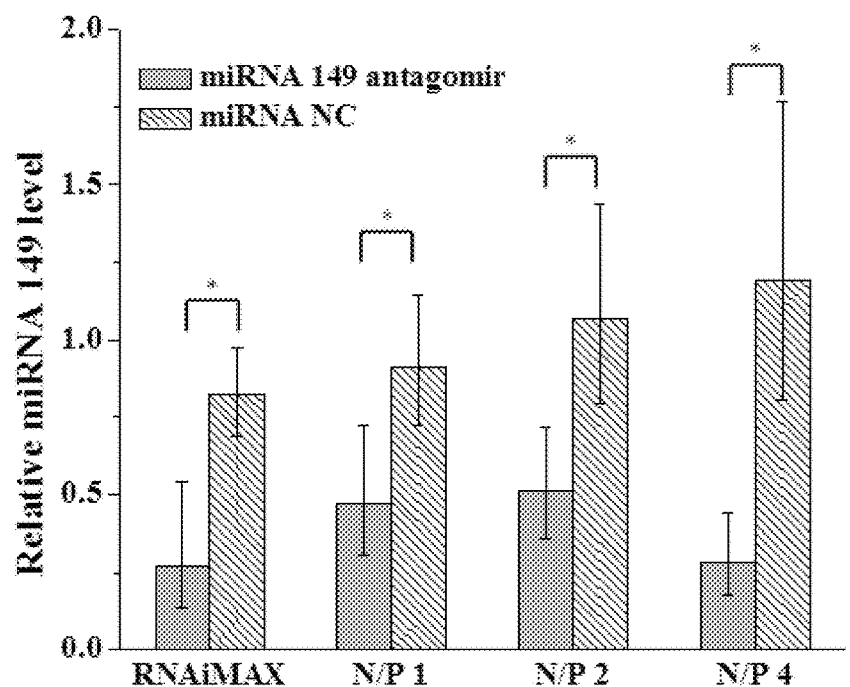

FIG. 11 is a graph showing relative miRNA 149 levels after 48-hour incubation with the indicated formulations. miRNAs of U6 was used as an internal standard, and all miRNA expression levels were normalized to control (no treatment). Error bars represent standard deviation of 4 replicates. * P<0.05

Figure 12:
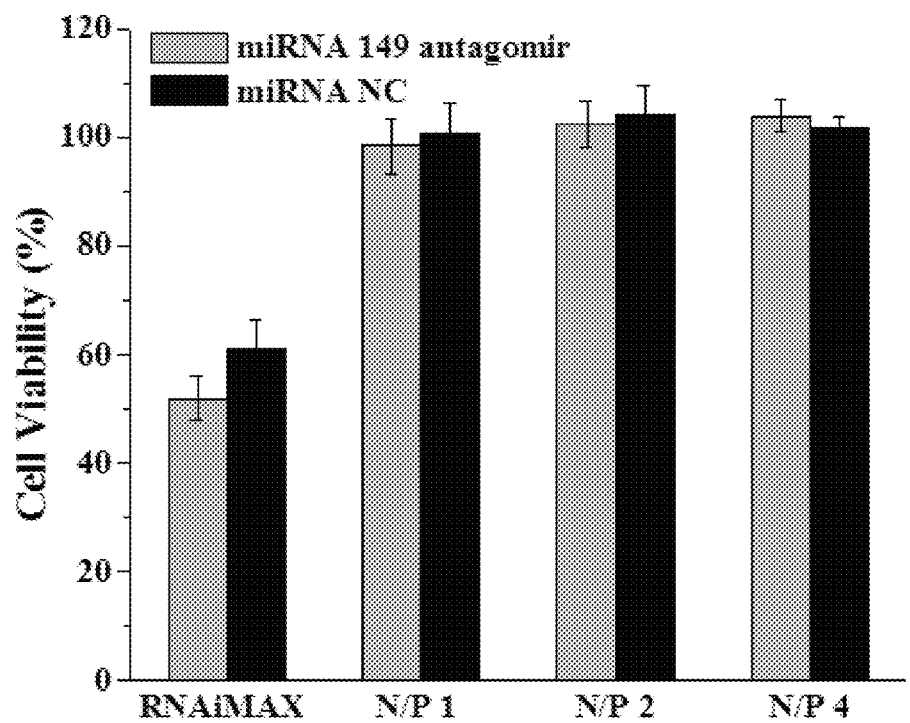

FIG. 12 is a graph showing results of cell viability of HepG2 cells after 24-hour incubation with different drug formulations: miRNA 149 inhibitor or miRNA NC complexed with Dex10-R$_5$H$_5$(40%) at N/P ratios of 1, 2 and 4, and miRNA 149 antagomir or miRNA NC complexed with RNAiMAX at designed ratio following its protocol.

DETAILED DESCRIPTION OF THE ILLUSTRATIVE EMBODIMENTS

In general, the novel compositions for nucleic acid delivery according to various embodiments of the present invention are directed to a group of polysaccharide polymers, having one or more nucleic acid delivery side chains comprising cationic peptides. In some embodiments, these cationic peptides condense and physically bond to nucleic acids to form a polysaccharide-nucleic acid complex that permits delivery to and transfection of the nucleic acid(s) into cells. In some embodiments, the polysaccharide polymers of the present invention may also have one or more zwitterionic side chains and/or reactive side chains.

The polysaccharide polymer composition for nucleic acid delivery according to various embodiments of the present invention comprises a polysaccharide polymer chain and one or more cationic peptides bonded to the polysaccharide polymer chain by means of a linker molecule, to form one or more nucleic acid delivery side chains. The polysaccharide polymer chain (also referred to herein as the polysaccharide polymer backbone or polymer backbone) is both biocompatible and biodegradable. In some embodiments, these polysaccharide polymer chains have one or more hydroxyl or amine groups available for the bonding of acrylate, methacrylate, methacrylamide, acrylamide, maleimide, haloacetyl, pyridyl disulfide and thiol groups. Suitable polysaccharide polymers include, without limitation dextran, cellulose, starch, glycosaminoglycans, mannan, dextrin, agar, agarose, alginic acid, alguronic acid, amylose, alpha glucan, amylopectin, beta-glucan, callose, carrageenan, cellodextrin, chitin, chitosan, chrysolaminarin, cyclodextrin, DEAE-sepharose, ficoll, fructan, fucoidan, galactoglucomannan, galactomannan, gellan gum, glucan, glucomannan, glucuronoxylan, glycocalyx, glycogen, hemicellulose, homopolysaccharide, hypromellose, inulin, laminarin, lentinan, levan polysaccharide, lichenin, mixed-linkage glucan, paramylon, pectic acid, pectin, pentastarch, phytoglycogen, pleuran, polydextrose, polysaccharide peptide, porphyran, pullulan, sepharose, xylan, xyloglucan, zymosan, hyaluronan, heparin, or combination thereof. In some embodiments, the polymer chain is a synthetic polymer, having one or more hydroxyl or amine groups available for the bonding of acrylate, methacrylate, methacrylamide, acrylamide, maleimide, haloacetyl, and pyridyl disulfide.

In one or more embodiments of the present invention, it is envisioned that the polysaccharide polymer chain of the present invention will have a relatively low weight average molecular weight, as it is believed that cytotoxicity increases as a function of molecular weight. On the other hand, it is envisioned that the weight average molecular weight of the polysaccharide polymer chain of the present invention not be too low, as to allow sufficient blood circulation time for the nucleic acid being carried to reach the target cells. In some embodiments, the polysaccharide polymer chain has a weight average molecular weight of from 500 daltons to about 10,000 daltons. In some embodiments, the polysaccharide polymer chain may have a weight average molecular weight of from 10,001 daltons to about 100,000 daltons. In some embodiments, the polysaccharide polymer chain may have a weight average molecular weight of from 100,001 daltons to about 500,000 daltons. In some embodiments, the polysaccharide polymer chain may have a weight average molecular weight of from 500,001 daltons to about 1,000,000 daltons.

In some embodiments, the polysaccharide polymer chain comprises dextran and has a weight average molecular weight of from 5,000 daltons to about 20,000 daltons. In some embodiments, the polysaccharide polymer chain comprises dextran and has a weight average molecular weight of from 5,000 daltons to about 50,000 daltons. In some embodiments, the polysaccharide polymer chain comprises dextran and has a weight average molecular weight of from 5,000 daltons to about 40,000 daltons. In some embodiments, the polysaccharide polymer chain comprises dextran and has a weight average molecular weight of from 5,000 daltons to about 25,000 daltons.

As set forth above, to the polysaccharide polymer chain are connected one or more nucleic acid delivery side chains. The nucleic acid delivery side chains are bonded to one or more hydroxyl or amine groups on the polysaccharide polymers forming the polysaccharide polymer chain and comprise a cationic peptide. It should be appreciated that the potential number of nucleic acid delivery side chains that can be added to the polysaccharide polymer chain will depend upon the particular polysaccharide polymer and is limited to the total number of binding sites in each glucose (or other monosaccharide) segment of the polysaccharide polymer chain. One glucose unit, for example, can have at most three nucleic acid delivery or other side chains. In some of these embodiments, the degree of substitution of the nucleic acid delivery side chains for polysaccharide polymer compositions according to one or more embodiment of the present invention may be from 0.1% to 50%. In some of these embodiments, the degree of substitution may be from 50% to 100%. In some of these embodiments, the degree of substitution may be from 100% to 200%. In some of these embodiments, the degree of substitution may be from 200% to 300%.

The composition of the nucleic acid delivery side chains according to one or more embodiment of the present invention is not particularly limited, provided that the material selected is capable of bonding to the polysaccharide polymer chain and includes a cationic peptide, as described above. The terms "nucleic acid delivery side chain" and "cationic peptide side chain" are used interchangeable herein to refer to a side chain having securing a cationic peptide to the polysaccharide polymer chain. In general, nucleic acid delivery side chains comprise a cationic peptide, as described above and linker molecule that links the cationic peptide to the polysaccharide polymer chain. In some embodiments, the linker molecule of the nucleic acid delivery side chains may comprise methacrylate, acrylate, methacrylate, methacrylamide, acrylamide, maleimide, haloacetyl, pyridyl disulfide, or a combination thereof. In some embodiments, linker molecule of the nucleic acid delivery side chains may comprise methacrylate.

As set forth above, in the polymer composition according to one or more embodiments of the present invention, a cationic peptide is bonded to an end of the nucleic acid delivery side chains distal to the polysaccharide polymer chain. As will be appreciated by those of ordinary skill in the art, a peptide is a short chain of amino acids linked by amide bonds. The covalent chemical bonds are formed when the carboxyl group of one amino acid reacts with the amino group of another amino acid. Amino acids that have been incorporated into peptides are termed "residues." Peptides are often classified according to the number of amino acid residues.

As set forth above, in some embodiments, the peptide of the present invention is a cationic peptide. As will be appreciated by those of skill in the art, certain amino acids, such as arginine, histidine, and lysine, have positively charged side chains that give the amino acid an overall positive charge. As used herein, the term "cationic peptide" refers a peptide having a sufficient number of positively charged amino acids to render all or a substantial portion of the peptide positively charged (cationic). The positively charged nature of the cationic peptide allows the peptide to be physically bound with the chosen nucleic acid. In addition, it has also been found that these cationic peptides cause the nucleic acid complexed thereto to condense.

In some embodiments, the cationic peptide of the present invention is also biocompatible and biodegradable. The term biocompatible is used in this manner to mean the ability of a material to perform with an appropriate host response in a specific situation. The term biodegradable is used in this manner to mean the chemical dissolution of a material by biological means, or a material being able to be degraded by cells/enzymes. In some embodiments, the peptide of the present invention may also contain histidine moieties so as to facilitate the endosomal escape of the nucleic acids being delivered to improve transfection efficiency.

The specific cationic peptide used is not particularly limited and any suitable cationic peptide may be used. It should be appreciated that suitable cationic will be able to condense and form physical bonds with nucleic acids peptides and linked, directly or indirectly to the polysaccharide polymer chain and may include, without limitation, a random copolymer having the formula $C_wR_5$, $C_wR_3H_3$, $C_wK_5$, $C_wK_3$, $C_wR_5H_5$, $C_wR_3H_3$, $C_wK_5H_5$, $C_wK_3H_3$, $C_wR_m$, $C_wK_n$, $C_wR_oH_p$, $C_wK_pH_q$, $C_wR_xK_yH_z$ or any combination of thereof; wherein C is cysteine, R is arginine, K is lysine, H is histidine, and m, n, o, p, q, x, y, z and w are integers from 1-1,000. In some embodiments, the cationic peptide may include, without limitation, a block copolymer having the formula $CR_5$, $CR_3H_3$, $CH_3R_3$, $CK_5$, $CK_3$, $CH_5R_5$ (SEQ. ID No. 1), $CR_5H_5$ (SEQ. ID No. 2), $CR_3H_3$, $CH_3R_3$, $CK_5H_5$ (SEQ. ID No. 3), $CH_5K_5$ (SEQ. ID No. 4), $CK_3H_3$, $CH_3K_3$, $R_5C$, $R_3H_3C$, $K_5C$, $K_3C$, $R_5H_5C$ (SEQ. ID No. 5), $R_3H_3C$, $K_5H_5C$ (SEQ. ID No. 6), $K_3H_3C$, $CR_m$, $CK_n$, $CR_oH_p$, $CK_pH_q$, $CR_xK_yH_z$, or the combination of thereof; wherein C is cysteine, R is arginine, K is lysine, H is histidine, and m, n, o, p, q, x, y, z and w are integers from 1-1,000. In some embodiments, the peptide is $R_5H_5$ (SEQ. ID No. 7). In some embodiments, the cationic peptide may have a terminal cysteine ("C") on the C terminal or N terminal of the peptide. In some embodiments, the peptide is $R_5H_5C$ (SEQ. ID No. 5).

The cationic peptide may be bonded to the rest of the nucleic acid delivery side chains in any manner known in the art. The particular method will, of course, depend upon the particular nucleic acid delivery side chain and cationic peptide involved. For example, in some embodiments, the nucleic acid delivery side chains are formed of methacrylate and a cationic peptide having the formula $NH_2$—RRRRRH-HHHHC—COOH ($R_5H_5C$) (SEQ. ID No. 5), having five arginine residues R, five histidine residues H and a terminal cysteine ("C") on the C terminal or N terminal end. In these embodiments, the thiol group on the terminal cysteine residue reacts with the methacrylate, thereby connecting the cationic peptide to the nucleic acid delivery side chain via a sulfur bond. In some other embodiments, the cationic peptide may be bound to the polysaccharide polymer chain by a methacrylamide, acrylamide, maleimide, haloacetyl, pyridyl disulfide, thiol or a combination thereof.

In some embodiments, the $R_5H_5C$ peptide was chosen because it has the ability to efficiently condense nucleic acids and to facilitate the endosomal escape of a DNA/vector complex to achieve high transition efficiency. $R_5H_5C$ was selected as a model peptide because it can condense DNA efficiently and it is representative of cationic peptides.

The polysaccharide polymer based nucleic acid delivery system of embodiments of the present invention is designed as a versatile platform, which can be readily conjugated with other functional groups to achieve dramatically improved therapeutic effects in the gene therapy. In some embodiments, for example, the polysaccharide polymer based nucleic acid delivery system of the present invention may further comprise one or more zwitterionic side chains chemically bonded to the polysaccharide polymer chain to increase the stability or the delivery efficiency of the delivery system.

The zwitterionic side chains of these embodiments of the present invention are bonded at one end to the polymer chain and contain a zwitterionic functional group. In some embodiments, the zwitterionic side chains are bonded to a glucose or other saccharide group in the polymer chain. (See Scheme 1, below) In some embodiments, the zwitterionic side chains may be bonded to the polysaccharide polymer backbone at an available hydroxyl, amide or carboxylate group.

In some embodiments, zwitterionic functional group may be a zwitterionic betaine group. In some embodiments, the zwitterionic functional group may be a carboxybetaine group, a sulfobetaine group, a phosphobetaine group or any combinations thereof. In some embodiments, the zwitterionic betaine may include, without limitation, 2-(di(methyl)(methylene)ammonio)acetate, 2-((methyl)(methylene)ammonio)acetate, 2-((methylene)ammonio)acetate 2-(bis(2-hydroxyethyl)(methylene)ammonio)acetate, 2-((2-hydroxyethyl)(methyl)ammonio)acetate, 2-((2-hydroxyethyl)(methylene)ammonia)acetate, 3-((methyl)(methylene)ammonio) propanoate, 3-(bi(methyl)(methylene)ammonio)propanoate, (bis(2-hydroxyethyl)(methylene)ammonio)propanoate, 3-((2-hydroxyethyl)(methylene)(methyl)ammonio)propanoate, 3-((2-hydroxyethyl)(methylene)ammonia) propanoate, or combinations and/or analogs and derivatives thereof.

In some embodiments, the zwitterionic betaine group may be separated from the polysaccharide polymer backbone by from 1 to 100 carbon, oxygen, nitrogen, or sulfur atoms. In some embodiments, the zwitterionic betaine group may be separated from the polysaccharide polymer backbone by from 1 to 10 carbon, oxygen, nitrogen, or sulfur atoms. In some embodiments, the zwitterionic betaine group may be separated from the polysaccharide polymer chain by from 11 to 50 carbon, oxygen, nitrogen, or sulfur atoms. In some embodiments, the zwitterionic betaine group may be separated from the polysaccharide polymer chain by from 51 to 100 carbon, oxygen, nitrogen, or sulfur atoms. In some embodiments, the zwitterionic side chains may comprise a carboxybetaine group having at least one ethanol, propanol, butanol or pentanol group bonded to the nitrogen atom of the carboxybetaine group.

Further, as shown below, it has been found that zwitterionic carboxybetaines with hydroxyl group(s) can switch between a cationic lactone (ring) form (II) (having antimicrobial properties) and the zwitterionic form (I) (having antifouling properties) and the intramolecular hydrogen bonds will enhance the mechanical properties of the polymer or hydrogel in which it is used. Under neutral or basic condition, these materials are in zwitterionic forms that have ultralow-fouling properties (I); and under acidic conditions, they will automatically convert into their cationic charged (ring) forms (II), which have excellent antimicrobial ability. Bacteria can be trapped and killed through contact, then released under neutral or basic environment. This process is reversible (switchable) by simply changing the acidic/basic environment of the medium.

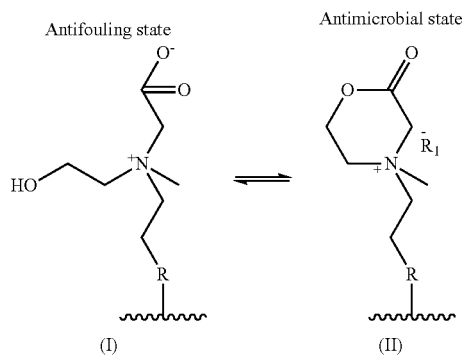

In some embodiments, the polymer composition of the present invention further comprises one or more reactive side chains. Like the zwitterionic side chains discussed above, the reactive side chains in these embodiments are bound at one end to the polysaccharide polymer chain. Suitable functional groups for use as part of the reactive side chains include, without limitation, maleimide, haloacetyl, pyridyl disulfide, thiol, methacrylate, acrylate, acrylamide and/or methacrylamide groups.

It should be appreciated that the potential number of side chains that can be added to the polysaccharide polymer chain will depend upon the particular polysaccharide and is limited to the total number of binding sites in each glucose (or other monosaccharide) segment of the polysaccharide polymer backbone. One glucose unit, for example, can have at most three, nucleic acid delivery, zwitterionic or reactive side chains. In some of these embodiments, the degree of substitution for the polymer composition may be from 0.1% to 300%. In some of these embodiments, the degree of substitution for polymer composition may be from 0.1% to 150%. In some of these embodiments, the degree of substitution for polymer composition may be from 0.1% to 100%. In some of these embodiments, the degree of substitution for polymer composition may be from 0.1% to 50%.

In some of these embodiments, the degree of substitution for the nucleic acid delivery side chains may be from 0.1% to 300%. In some of these embodiments, the degree of substitution for nucleic acid delivery side chains may be from 0.1% to 150%. In some of these embodiments, the degree of substitution for nucleic acid delivery side chains may be from 0.1% to 100%. In some of these embodiments, the degree of substitution for nucleic acid delivery side chains may be from 0.1% to 50%.

In some of these embodiments, degree of substitution for zwitterionic side chains in compositions according to embodiments of the present invention may be from 0.1% to 300%. In some embodiments, degree of substitution for zwitterionic side chains in compositions according to embodiments of the present invention may be from 0.1% to 50%. In some embodiments, degree of substitution for zwitterionic side chains in compositions according to embodiments of the present invention may be from 0.1% to 100%. In some embodiments, degree of substitution for zwitterionic side chains in compositions according to embodiments of the present invention may be from 0.1% to 150%. In some embodiments, degree of substitution for zwitterionic side chains in compositions according to embodiments of the present invention may be from 1% to 20%.

In some of these embodiments, degree of substitution for reactive side chains in compositions according to embodiments of the present invention may be from 0.1% to 300%. In some embodiments, degree of substitution for reactive side chains in compositions according to embodiments of the present invention may be from 0.1% to 50%. In some embodiments, degree of substitution for reactive side chains in compositions according to embodiments of the present invention may be from 0.1% to 100%. In some embodiments, degree of substitution for reactive side chains in compositions according to embodiments of the present invention may be from 0.1% to 150%. In some embodiments, degree of substitution for reactive side chains in compositions according to embodiments of the present invention may be from 1% to 20%.

The size of the polymer compositions according to embodiments of the present invention is not particularly limited and will depend upon the particular composition and its intended use. In some embodiments, the composition of the present invention may have a weight average molecular weight of from 300 to 10,000,000 daltons. In some embodiments, the polymer composition of the present invention may have a weight average molecular weight of from 300 to 1,000,000 daltons. In some embodiments, the polymer composition of the present invention may have a weight average molecular weight of from 300 to 100,000 daltons. In some embodiments, the polymer composition of the present invention may have a weight average molecular weight of from 300 to 10,000 daltons. In some embodiments, the polymer composition of the present invention may have a weight average molecular weight of from 4000 to 10,000 daltons.

In some aspects, the present invention is directed to a complex comprising the polysaccharide polymer composition for nucleic acid delivery described above and a nucleic acid to be used in gene therapy. In these embodiments, the polysaccharide polymer composition described above acts as a carrier of the nucleic acids being delivered for gene therapy. Nucleic acids are polymeric macromolecules essential for all known forms of life. Nucleic acids, which include DNA (deoxyribonucleic acid), RNA (ribonucleic acid) or their derivatives (such as Locked Nucleic Acid), are made from monomers known as nucleotides. Each nucleotide has three components: a 5-carbon sugar, a phosphate group, and a nitrogenous base. If the sugar is deoxyribose, the nucleic acid is DNA. If the sugar is ribose, the nucleic acid is RNA. Locked Nucleic Acid is a novel type of nucleic acid analog containing a 2'-O, 4'-C methylene bridge—See http://www.sigmaaldrich.com/technical-documents/articles/biology/locked-nucleic-acids-faq.html#sthash.pnRVQSq4.dpuf, the disclosure of which is incorporated herein by reference in its entirety.

The particular nucleic acid to be delivered is chosen based on the type of gene to be regulated. The particular nucleic acid can either be used to suppress the activity of the gene, or in some cases, it may be beneficial for the nucleic acid to enhance the activity of the gene. In some embodiments, nucleic acids can also be used to inhibit gene expression in human cells. For example, RNA molecules can under a biological process known as RNA interference. RNA interference (RNAi) is a biological process in which RNA molecules inhibit gene expression, typically by causing the destruction of specific mRNA molecules. Four types of small ribonucleic acid (RNA) molecules—microRNA (miRNA), small interfering RNA (siRNA) and Short Hairpin RNA (shRNA)—are central to RNA interference. RNAs are the direct products of genes, and these small RNAs can bind to other specific messenger RNA (mRNA) molecules and either increase or decrease their expression level, for example by preventing an mRNA from producing a protein. RNA interference has an important role in defending cells against parasitic nucleotide sequences—viruses and transposons. It also influences development as well as being able to suppress the activity of proteins responsible for cellular defense induced by chemotherapy agents, such as anticancer drugs.

Small interfering RNA (siRNA), sometimes known as short interfering RNA or silencing RNA, is a class of double-stranded RNA molecules, 20-25 base pairs in length. siRNA plays many roles, but it is most notable in the RNA interference (RNAi) pathway, where it interferes with the expression of specific genes with complementary nucleotide sequences. siRNA functions by causing mRNA to be broken down after transcription, resulting in no translation. MicroRNAs (miRNAs) are non-coding RNAs that play critical roles in a broad range of biologic processes, including differentiation, proliferation, cell cycle regulation and apoptosis. MiRNA expression is commonly deregulated in almost all types of diseases, including cancers. MiRNAs aberrantly express during cancer development, invasion and metastasis, and function as either oncogenes or tumor suppressors.

In some embodiments, the nucleic acid to be delivered by the polymer composition of the present invention may include, without limitation, Plasmid DNA, Oligonucleotides, Aptamers, DNAzymes, RNA Aptamers, RNA Decoys, Antisense RNA, Ribozymes, Small Interfering RNAs, MicroRNAs (miRNA), siRNA, or Antagomirs. In some embodiments, the nucleic acid is Plasmid DNA. In some embodiments, the nucleic acid is a siRNA. In some embodiments, the nucleic acid is a miRNA.

As will be appreciated by those of ordinary skill in the art, the phosphorous atoms of the nucleic acid are negatively charged and are electrostatically attracted to the positively charged (cationic) peptide. Among other things, the strength of the bond formed between the nucleic acid and cationic peptide is a function of the N/P ration of the complex. As used herein, the term N/P ratio refers to the molar ratio of amine or guanidine group on the side chain of peptide to the phosphorous group on nucleic acids. In some embodiments, the N/P ratio of the polymer/nucleic acid complex of the present invention may be between 0.1 and 1. In some embodiments, the N/P ratio of the polymer/nucleic acid complex of the present invention may be between 1 and 5. In some embodiments, the N/P ratio of the polymer/nucleic acid complex of the present invention may be between 5 and 10. In some embodiments, the N/P ratio of the polymer/nucleic acid complex of the present invention may be between 10 and 40. In some embodiments, the N/P ratio of the polymer/nucleic acid complex of the present invention may be between 1 and 100.

Particle size and surface charge are two important factors that influence transfection efficiency of the gene delivery compositions of the present invention. As set forth above, the cationic peptide on the nucleic acid delivery side chains of embodiments of the present invention will cause the nucleic acid complexed thereto to condense. It has been found that the degree to which the nucleic acid will be condensed by the cationic peptide depends upon N/P ratios, molecular weight of the polymer and charge density of the polymer. As used here, the term particle size refers to the hydrodynamic size of the particle in solution, which is measured by dynamic light scattering techniques. In some embodiments, the particle size of the polymer/nucleic acid complex of the present invention may be between 1 nm and 10 nm. In some embodiments, the particle size of the polymer/nucleic acid complex of the present invention may be between 10 nm and 50 nm. In some embodiments, the particle size of the polymer/nucleic acid complex of the present invention may be between 50 nm and 200 nm. In some embodiments, the particle size of the polymer/nucleic acid complex of the present invention may be between 200 nm and 3,000 nm.

As used herein, the terms "surface charge" and/or "zeta potential" are interchangeable and refer to the electric potential in the interfacial double layer (DL) at the location of the slipping plane relative to a point in the bulk fluid away from the interface. In some embodiments, the surface charge of the polymer/nucleic acid complex of the present invention may be between −5 mV and 0 mV. In some embodiments, the surface charge of the polymer/nucleic acid complex of the present invention may be between 0 mV and 5 mV. In some embodiments, the surface charge of the polymer/nucleic acid complex of the present invention may be between 5 mV and 15 mV. In some embodiments, the surface charge of the polymer/nucleic acid complex of the present invention may be between 15 mV and 50 mV.

In another aspect, embodiments of the present invention are directed to a method for forming the novel polysaccharide polymer compositions discussed above. In some embodiments, the novel polysaccharide polymer compositions discussed above may be synthesized via the reaction shown in Scheme 1, below.

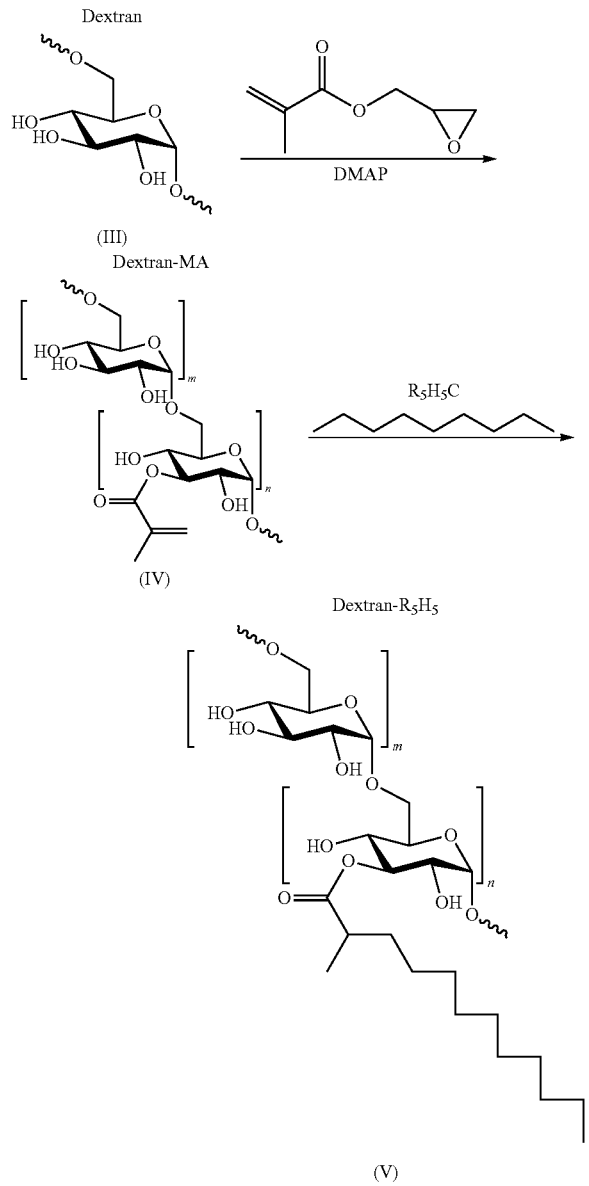

The method begins with selecting and/or preparing any one or more of the polysaccharide polymer chain described above. As set forth above, these polymers should have one or more hydroxyl and/or amine groups available for bonding. A suitable polysaccharide polymer chain, for example, may comprise saccharides such as dextran, cellulose, starch, glycosaminoglycans, mannan, dextrin, agar, agarose, alginic acid, alguronic acid, amylose, alpha glucan, amylopectin, beta-glucan, callose, carrageenan, cellodextrin, chitin, chitosan, chrysolaminarin, cyclodextrin, DEAE-sepharose, ficoll, fructan, fucoidan, galactoglucomannan, galactomannan, gellan gum, glucan, glucomannan, glucuronoxylan, glycocalyx, glycogen, hemicellulose, homopolysaccharide, hypromellose, inulin, laminarin, lentinan, levan polysaccharide, lichenin, mixed-linkage glucan, paramylon, pectic acid, pectin, pentastarch, phytoglycogen, pleuran, polydextrose, polysaccharide peptide, porphyran, pullulan, sepharose, xylan, xyloglucan, zymosan, hyaluronan, heparin, and/or combinations thereof.

In some embodiments, the nucleic acid side chains may be added to the selected polysaccharide polymer using a two-step reaction, as shown in Scheme 1 above. In these embodiments, the selected polysaccharide polymer chain is dissolved in a suitable solvent. The suitability of the solvent will, of course, depend upon the specific polymer selected, but one of ordinary skill in the art will be able to select a suitable solvent without undue experimentation. In the embodiments shown in Scheme 1, the polymer chain is dextran (III) and it is dissolved in dimethyl sulfoxide (DMSO).

In some other embodiments the polymer chain may be cellulose, starch, glycosaminoglycans, mannan, dextrin, agar, agarose, alginic acid, alguronic acid, amylose, alpha glucan, amylopectin, beta-glucan, callose, carrageenan, cellodextrin, chitin, chitosan, chrysolaminarin, cyclodextrin, DEAE-sepharose, ficoll, fructan, fucoidan, galactoglucomannan, galactomannan, gellan gum, glucan, glucomannan, glucuronoxylan, glycocalyx, glycogen, hemicellulose, homopolysaccharide, hypromellose, inulin, laminarin, lentinan, levan polysaccharide, lichenin, mixed-linkage glucan, paramylon, pectic acid, pectin, pentastarch, phytoglycogen, pleuran, polydextrose, polysaccharide peptide, porphyran, pullulan, sepharose, xylan, xyloglucan, zymosan, hyaluronan heparin or a combination thereof.

In the embodiment shown in Scheme 1, the dextran (III) is then reacted with glycidyl methacrylate (GMA) in the presence of 4-(dimethylamino)pyridine (DMAP) to functionalize the dextran (III) with methacrylate via transesterification of the methacryloyl group of the GMA to dextran (III), yielding Dextran-MA (IV) (Dex-MA). In some other embodiments, the polysaccharide polymer chain may be functionalized with methacrylic acid, acrylic acid, a compound with maleimide at one end and carboxylic acid group at the other end, or a compound with haloacetyl or pyridyl disulfide at one end and carboxylic acid group at the other end. In the embodiment shown in Scheme 1, DMAP is used to catalyze the transesterification reaction. Other suitable catalysts may include, without limitation, triethylamines, pyridine, Hünig's Base, DSU, or Barton's Base. In some embodiments, the Dex-MA polymers may be made as set forth in Example 1.

In a second step, a cationic peptide, such as those described above, is added to one or more of the methacryloyl (or acrylate, methacrylate, methacrylamide, acrylamide, maleimide and/or haloacetyl) groups now bonded to the polysaccharide polymer chain to form the cationic peptide side chains described above. The cationic peptide may be any of the cationic peptides described above. In the embodiment of Scheme 1, the cationic peptide is a $R_5H_5$ peptide with a C-terminal cysteine residue and it is conjugated to Dex-MA via the thiol-methacrylate Michael type reaction at pH 8.0, to form Dextran-$R_5H_5$ (V) (Dex-$R_5H_5$). To have a high charge density and low steric hindrance at conjugation, the cysteine residue may be put at the C-terminal of the peptide. With this approach, no further modification of the peptide is needed and it can be adapted to conjugate any peptide with cysteine residue(s). In some embodiments, the Dex-$R_5H_5$ polymers may be made as set forth in Example 2.

In other embodiments, the cationic peptide may be added to one or more of the methacryloyl (or acrylate, methacrylate, methacrylamide, acrylamide or maleimide) groups now bonded to the polysaccharide polymer chain in the presence of free radical initiator by means of a thiol-ene reaction to form the cationic peptide chains described above. Again, to have a high charge density and low steric hindrance at conjugation, the cysteine residue may be put at the C-terminal of the peptide. With this approach, no further modification of the peptide is needed and it can be adapted to conjugate any peptide with cysteine residue(s).

As set forth above, in some embodiments, the polysaccharide polymer based nucleic acid delivery system of embodiments of the present invention may further comprise one or more zwitterionic side chains chemically bonded to the polysaccharide polymer chain to increase the stability or the delivery efficiency of the delivery system. (See Scheme 2, below) In some embodiments, these polymers may be made as shown in Scheme 2 below. In these embodiments, the polysaccharide polymer chain is first modified with one or more zwitterionic side chains as shown in step A of Scheme 2, below. In the embodiment of Scheme 2, polysaccharide polymer chain is comprised of dextran (III) and is reacted with N,N-Dimethylglycine ethyl ester and epichlorohydrin to add a zwitterionic betaine group to one of the hydroxyl groups of the dextran to form CB-Dex (VI). In some embodiments, CB-Dex may be synthesized as set forth in Example 11, below. The nucleic acid delivery side chains are added the CB-Dex as shown in steps B and C of Scheme 2 and/or as set forth above. In the embodiment of Scheme 2 (step B), the CB-Dex is reacted with GMA and DMAP to add the methacrylate group to the CB-Dex to form CB-Dex-MA (VII). In some embodiments, the polysaccharide polymer chain having one or more zwitterionic side chains may be subsequently modified with methacrylate, acrylate, methacrylate, methacrylamide, acrylamide, maleimide, haloacetyl, and pyridyl disulfide, thiol or a combination of thereof. Last, the cationic peptide is added to the functionalized polysaccharide polymer chain as described above and shown in step C of Scheme 2.

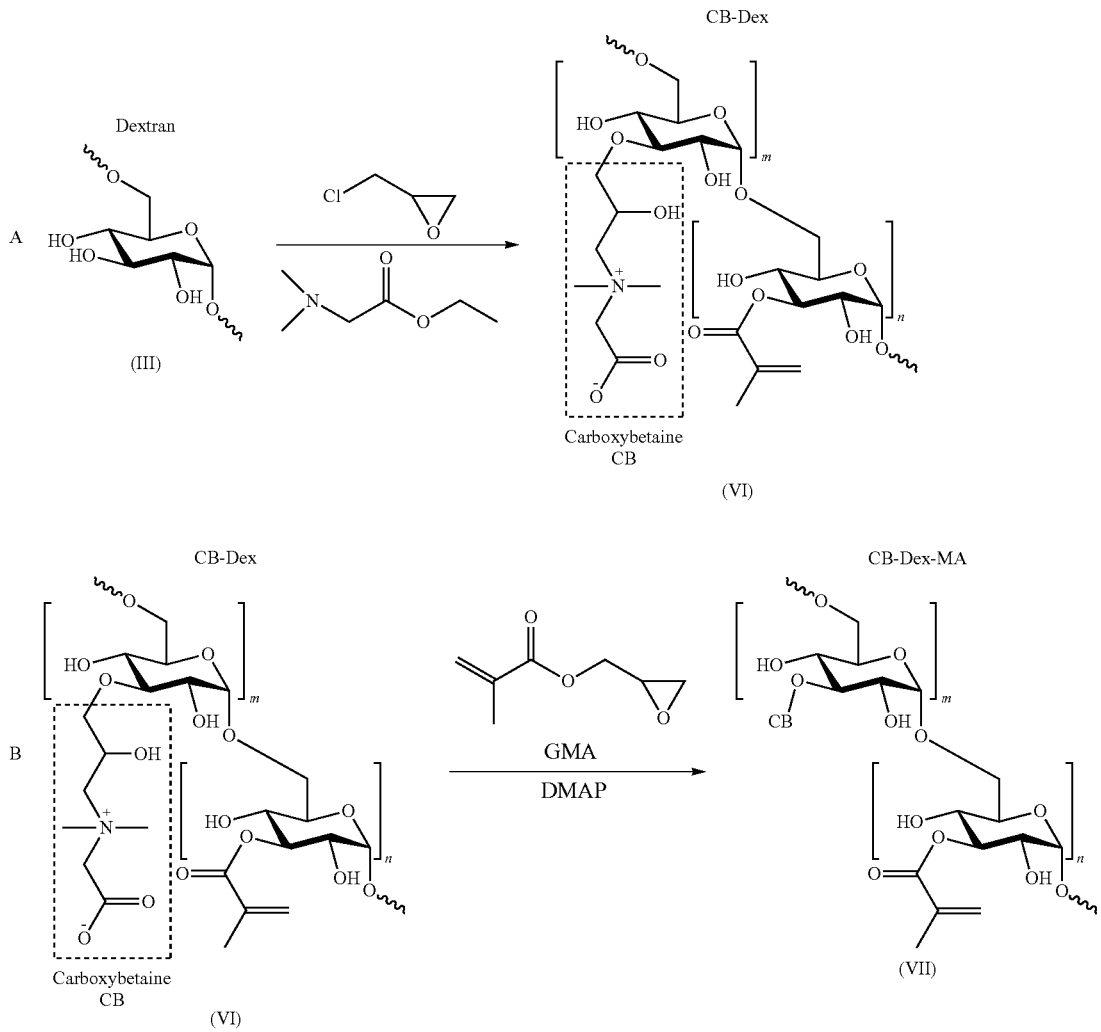

Scheme 2

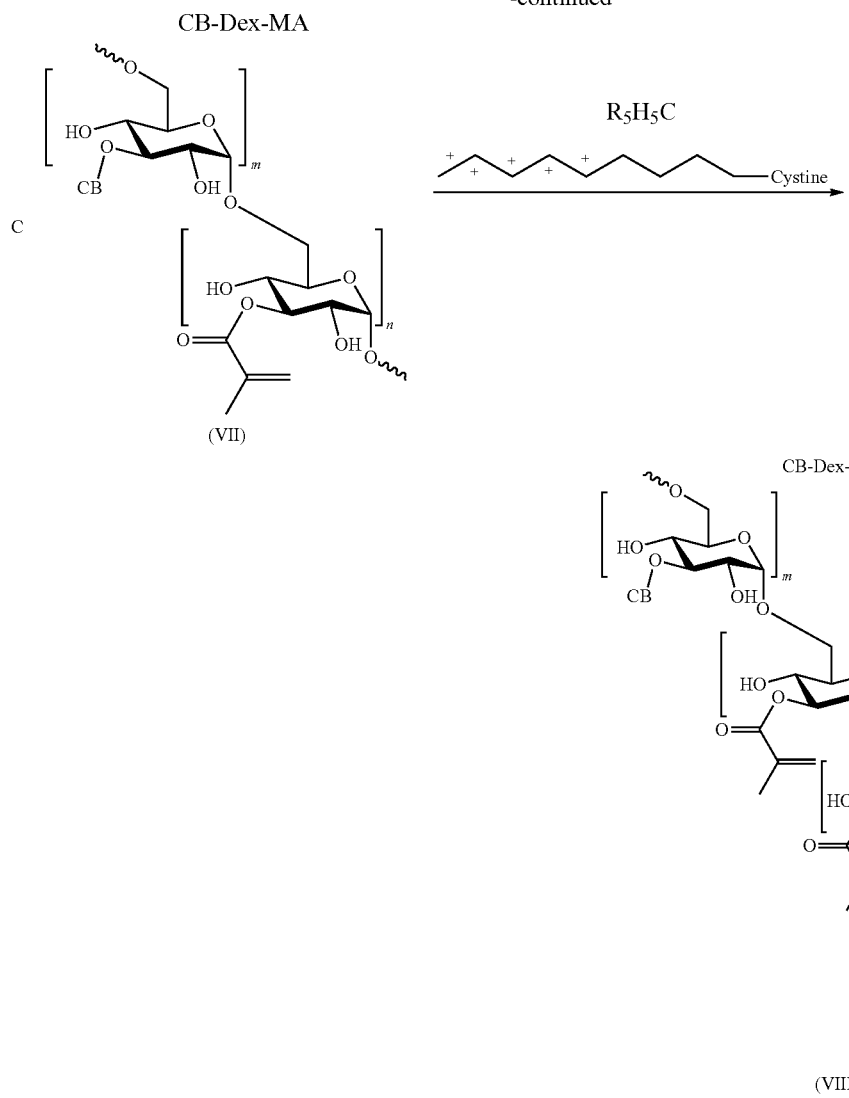

As set forth above, the one or more zwitterionic side chains will have a zwitterionic functional group. In some embodiments, zwitterionic functional group may be a zwitterionic betaine group. In some embodiments, the zwitterionic functional group may be a carboxybetaine group, a sulfobetaine group, a phosphobetaine group or any combinations thereof. In some embodiments, the zwitterionic betaine may include, without limitation, 2-(di(methyl)(methylene)ammonio)acetate, 2-((methyl)(methylene)ammonio)acetate, 2-((methylene)ammonio)acetate 2-(bis(2-hydroxyethyl)(methylene)ammonia)acetate, 2-((2-hydroxyethyl)(methylene)(methyl)ammonio)acetate, 2-((2-hydroxyethyl)(methylene)ammonio)acetate, 3-((methyl)(methylene)ammonia) propanoate, 3-(bi(methyl)(methylene)ammonio)propanoate, 3-(bis(2-hydroxyethyl)(methylene)ammonio)propanoate, 3-((2-hydroxyethyl)(methylene)(methyl)ammonio)propanoate, 3-((2-hydroxyethyl)(methylene)ammonio) propanoate, or combinations and/or analogs and derivatives thereof.

In these embodiments, the zwitterionic compound will also have at least one functional group configured to bond to the polymer chain and at least one zwitterionic functional group. It should be appreciated that the zwitterionic compound may be any of the zwitterionic side chains discussed above, functionalized to bond to the polymer backbone. Further, the functional group or groups configured to bond to the polymer chain will, of course, depend upon the particular polymer backbone used but may include, without limitation, epoxide, ester, alkyl halide, acyl halide, carboxylate, sulfonate and aldehyde. In the embodiment shown above in Scheme 2, for example, an epoxide functional group on the zwitterionic compound was reacted with one of the available hydroxyl groups on the polysaccharide polymer backbone to bond the zwitterionic compound to the polymer backbone, thus forming a zwitterionic side chain as described above.

The suitability of the organic or inorganic base will, of course, depend upon the specific polymer and zwitterionic compound selected, but one of ordinary skill in the art will be able to select a suitable organic or inorganic base without undue experimentation. In some embodiments, for example, the polymer chain is a polysaccharide such as dextran and the zwitterionic side chain is a carboxybetaine or glycine betaine. In these embodiments, suitable organic or inorganic base(s) may include without limitation sodium carbonate, pyridine, triethyl amine, Hünig's Base, 1,8-Diazabicyclo [5.4.0]undec-7-ene, Barton's Base and sodium hyzide.

In some embodiments, a polysaccharide polymer chain may be reacted with an ester derivative of zwitterionic betaine that contains one tertiary amine, and dibromoalkane, dichloroalkane, diepoxide, multi halide substituted alkane, or multi halide epoxide substituted alkane to produce a cationic polysaccharide composition and then hydrolyzed in suitable acidic or basic conditions to produce a polysaccharide polymer chain having one or more zwitterionic polymer side chains. In some embodiments, the zwitterionic compound may be a an ester derivative of zwitterionic betaine that contains a primary amine, secondary amine or tertiary amine, and a dibromoalkane, dichloroalkane, diepoxide, epichlorohydrin, a molecule with an acyl halide at one end and halide on the other end, a multi halide substituted alkane, a multi epoxide substituted alkane or a multi halide and epoxide substituted alkane. As one of ordinary skill in the art will appreciate, the selection of a suitable acid or a suitable base to hydrolyze the cationic polysaccharide will depend on the type of ester group on the cationic polysaccharide to be hydrolyzed. A methyl, ethyl, or propyl ester, for example, may be hydrolyzed under basic conditions to produce the polysaccharide polymer chain having one or more zwitterionic polymer side chains. A butyl ester, on the other hand, may be hydrolyzed under acid conditions to produce the polysaccharide polymer chain having one or more zwitterionic polymer side chains.

In some embodiments, the zwitterionic compound may be a zwitterionic betaine carrying one primary amine, secondary amine or tertiary amine, and a dibromoalkane, dichloroalkane, diepoxide, multi epoxide substituted alkane, multi halide substituted alkane, or a combination thereof. In some embodiments, the zwitterionic betaine comprises a carboxybetaine group. In some embodiments, the zwitterionic betaine may be 2-(di(methyl)(methylene)ammonio)acetate, 2-((methyl)(methylene)ammonio)acetate, 2-((methylene) ammonio)acetate 2-(bis(2-hydroxyethyl)(methylene)ammonio)acetate, 2-((2-hydroxyethyl)(methylene)(methyl)ammonio)acetate, 2-((2-hydroxyethyl)(methylene)ammonio) acetate, 3-((methyl)(methylene)ammonio) propanoate, 3-(bi (methyl)(methylene)ammonio)propanoate, 3-(bis(2-hydroxyethyl)(methylene)ammonio)propanoate, 3-((2-hydroxyethyl)(methylene)(methyl)ammonio)propanoate, 3-((2-hydroxyethyl)(methylene)ammonio)propanoate, and/ or combinations or analogs/derivatives thereof.

In some embodiments, the polysaccharide polymer chain may be reacted with dimethylglycine and epichlorohydrin in the presence of an organic and inorganic base and then hydrolyzed in acidic or basic conditions to produce to produce a polysaccharide polymer chain having one or more zwitterionic polymer side chains. In some embodiments, the polysaccharide polymer chain may be reacted with 3-bromopropanoyl bromide or 2-bromoacetyl bromine and a zwitterionic betaine carrying a tertiary amine in the presence of an organic and inorganic base and then hydrolyzed in acidic or basic conditions to produce to produce a polysaccharide polymer chain having one or more zwitterionic polymer side chains. In some embodiments, the polysaccharide polymer chain may be reacted with 3-bromopropanoyl bromide or 2-bromoacetyl bromine and ester derivative of zwitterionic betaine carrying a tertiary amine in the presence of an organic and inorganic base and then hydrolyzed in acidic or basic conditions to produce to produce a polysaccharide polymer chain having one or more zwitterionic polymer side chains.

Once all of the side chains have been added, the polymer composition may be purified according to any suitable method known in the art for that purpose. In some embodiments, polymer compositions may be purified using a dialysis membrane or by precipitation of the polymer composition into ethanol, ether, or another suitable organic solvent. The resulting polysaccharide polymer composition may then be dried according to any suitable method known in the art for that purpose. In some embodiments, the polymer composition may then be dried by lyophilizing. In some embodiments, the polymer composition may then be dried by lyophilization, vacuum, or heat.

EXPERIMENTAL

To evaluate the effect of the molecular weight of the polymer backbone on the transfection efficiency at various degrees of substitution, dextran with three different molecular weights (10, 20 and 70 kDa) was conjugated with an oligopeptide $NH_2$—RRRRRHHHHHC—COOH ($R_5H_5C$) (SEQ ID No. 5) to form Dex-$R_5H_5$ at various substitution degrees. See Examples 1-3. As set forth above, dextran, a natural biodegradable polysaccharide is widely used as polymeric carriers in drug delivery systems. The presence of high amount of hydroxyl groups in dextran enable the efficient incorporation of other functional molecules into the polymer backbone. Dextran conjugated with polyethylenimine (PEI), an efficient transfection reagent, is reported to reduce the toxicity of PEI and increase its stability in the presence of serum. It has been demonstrated that $R_5H_5$ can effectively condense nucleic acids binding via arginine residues and facilitate endosomal escape via histidine residues, and was used here as cationic peptide block of the polysaccharide polymer composition for nucleic acid delivery of embodiments of the present invention. See, Tang, Q.; Cao, B.; Wu, H. Y.; Cheng, G., Cholesterol-Peptide Hybrids to Form Liposome-Like Vesicles for Gene Delivery, *Plos One* 2013, 8, (1), the disclosure of which is encorporated herein by reference in its entirety. The utility of the dextran-peptides of embodiments of the present invention for gene condensation and gene delivery was investigated in a human ovarian carcinoma cell line SKOV-3, in comparison with that of 25 kDa PEI.

Figure 1:
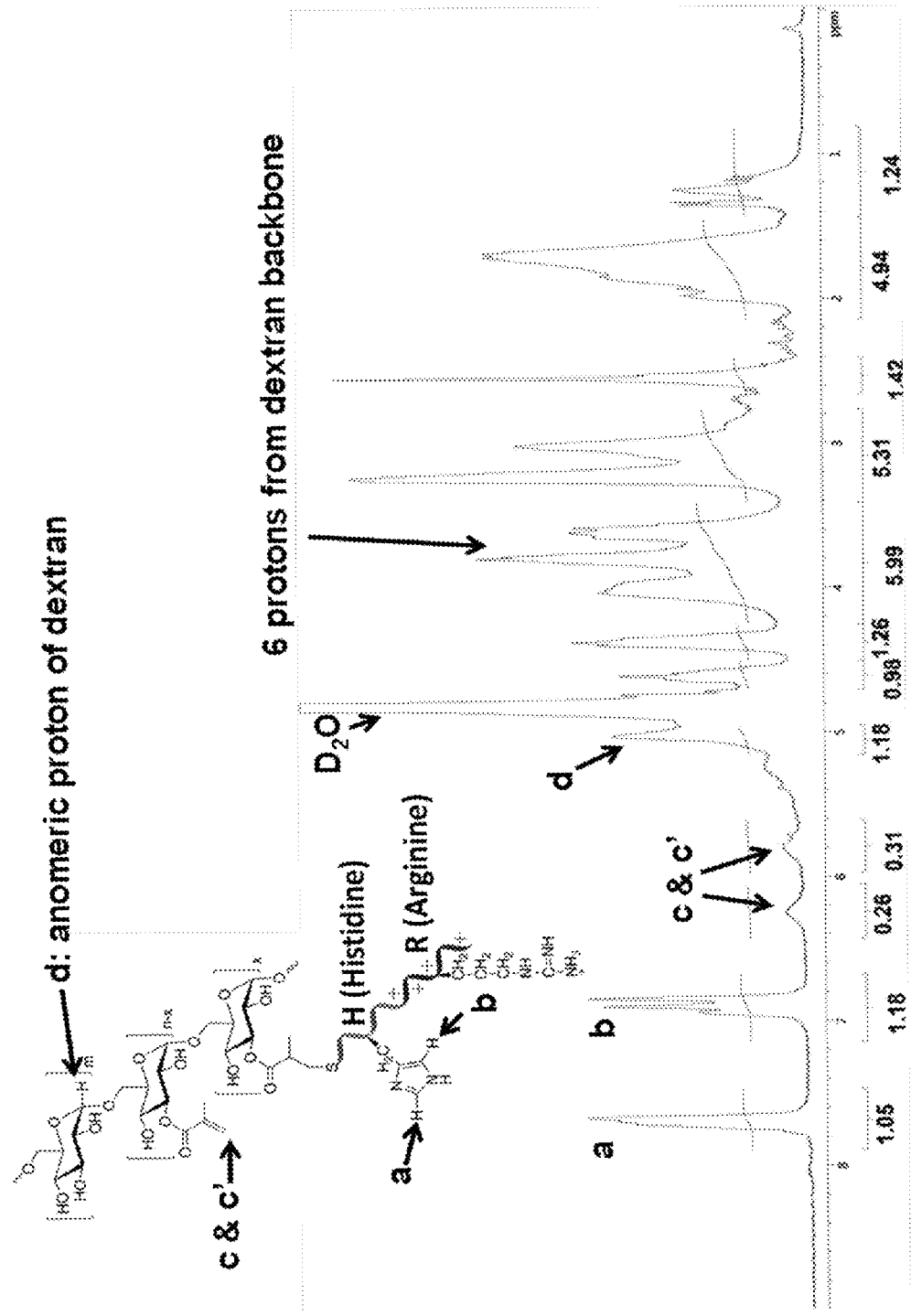
FIG. 1 is a 300 MHz $^1$H NMR spectrum of Dex10-$R_5H_5$ (20%) according to one or more embodiment of the present invention in $D_2O$.
Figure 2:
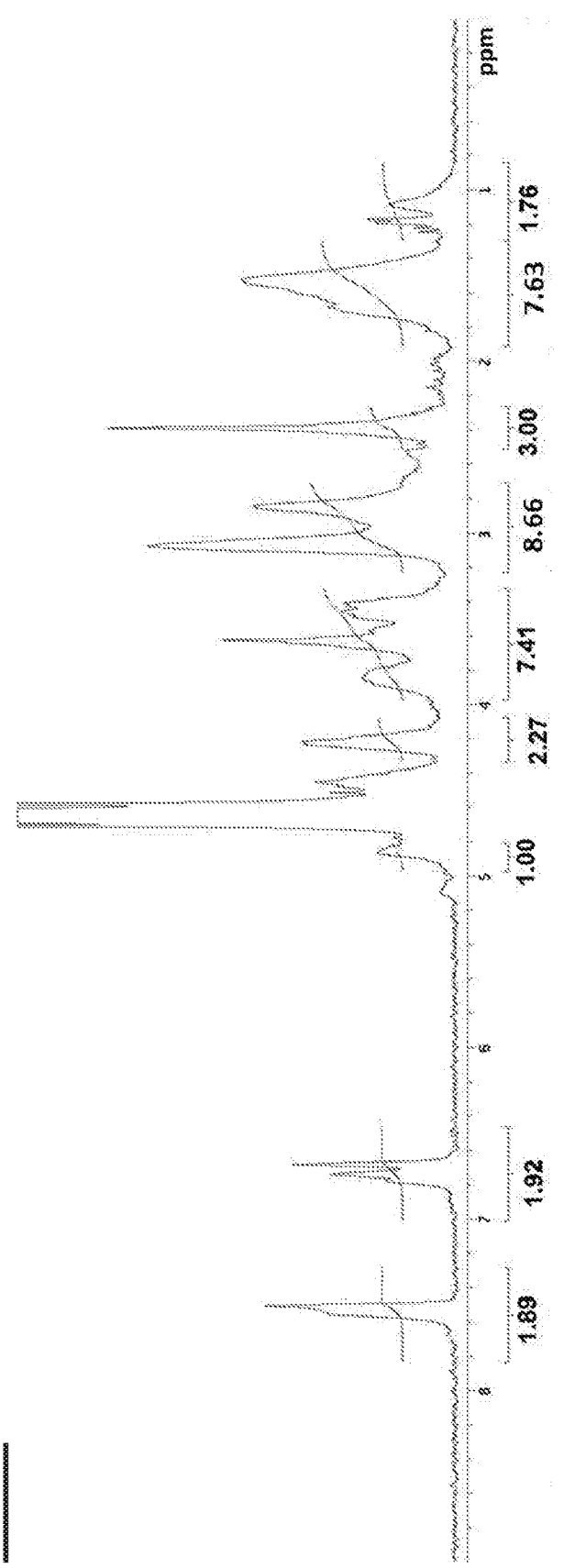
FIG. 2 is a 300 MHz $^1$H NMR spectrum of Dex10-$R_5H_5$ (40%) according to one or more embodiment of the present invention in $D_2O$.
Figure 3:
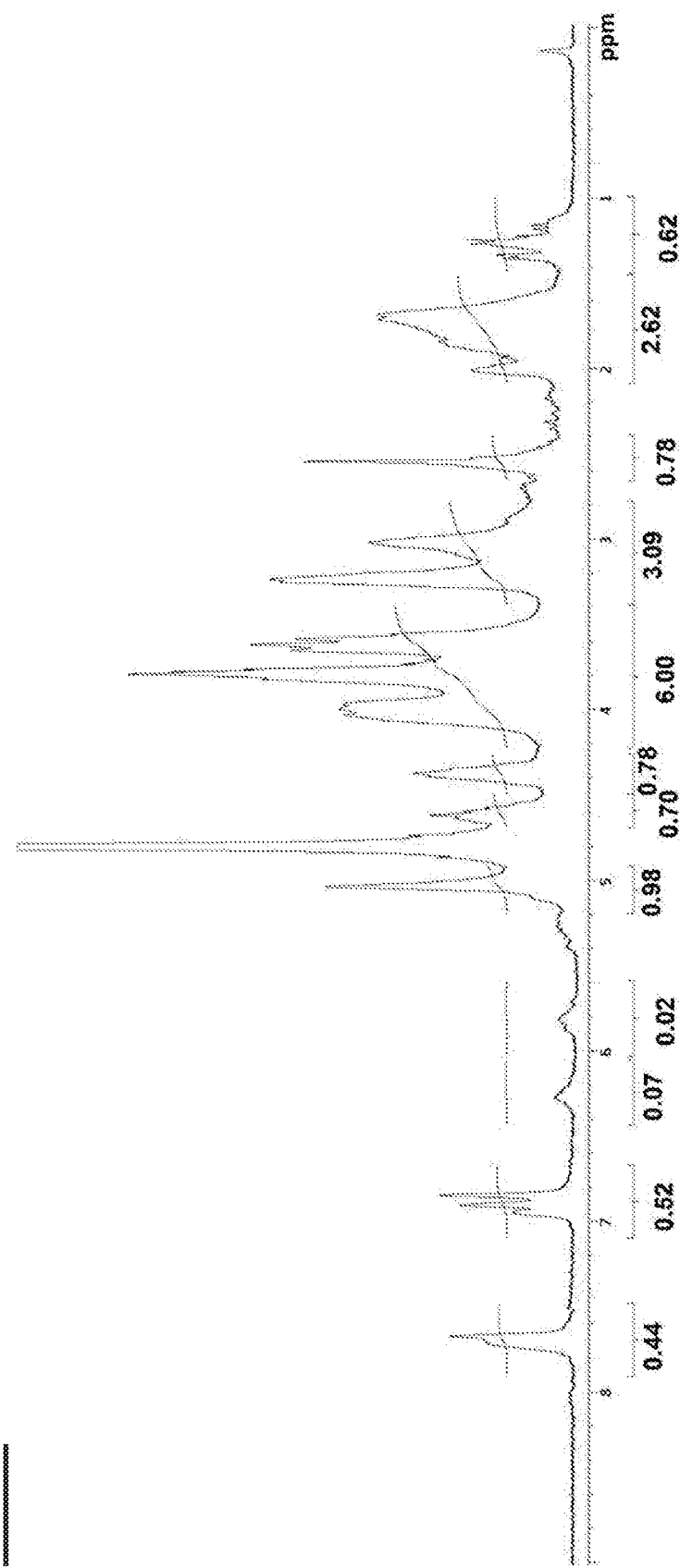
FIG. 3 is a 300 MHz $^1$H NMR spectrum of Dex20-$R_5H_5$ (10%) according to one or more embodiment of the present invention in $D_2O$.
Figure 4:
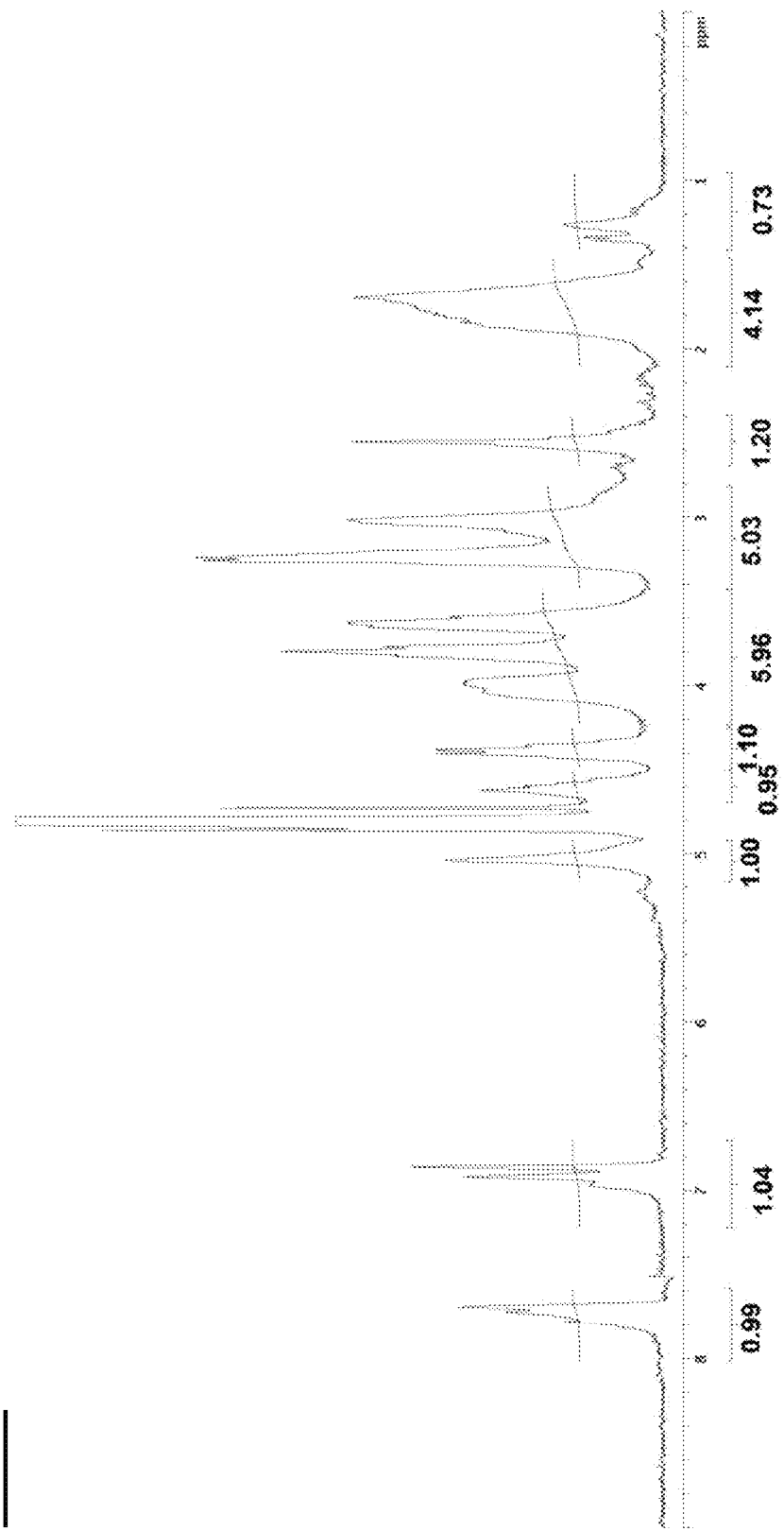
FIG. 4 is a 300 MHz NMR spectrum of Dex20-$R_5H_5$ (20%) according to one or more embodiment of the present invention in $D_2O$.
Figure 5:
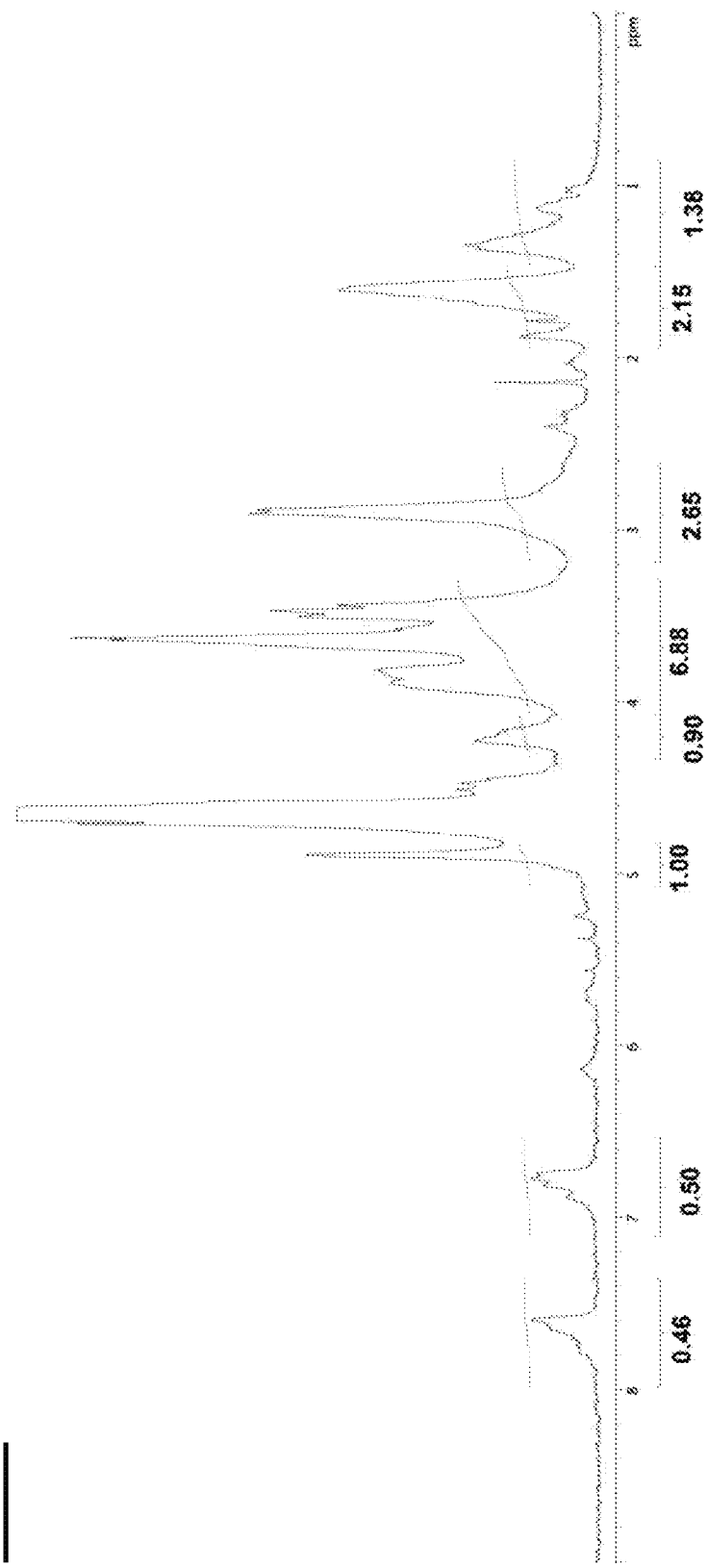
FIG. 5 is a 300 MHz $^1$H NMR spectrum of Dex70-$R_5H_5$ (10%) according to one or more embodiment of the present invention in $D_2O$.]

Dex-$R_5H_5$ hybrids polymers were prepared as described above and in Example 1 below using dextran polymer chains with average molecular weight of 10, 20 and 70 kDa. The structure of these Dex-$R_5H_5$ hybrids was studied by $^1$H-NMR (See FIGS. 1-5). The DS of $R_5R_5$ was calculated by integration of the anomeric protons of dextran (5.0 ppm), and the integration of protons from imidazole ring of histidine (6.9 and 7.7 ppm). Because of the overlap with solvent peak in some cases, integration of the anomeric proton peak is very difficult, so that resonance of six protons from dextran backbone (from 3.4 to 4.1 ppm) was used as a reference to verify the accuracy of the calculation. Peaks used for calculations have been assigned in the $^1$H NMR spectrum as shown in FIG. 1. The $^1$H-NMR confirm that five Dex-$R_5H_5$ hybrids with different molecular weight and degree of substitution (DS), Dex10-$R_5H_5$ (20%), Dex10-$R_5H_5$ (40%), Dex20-$R_5H_5$ (10%), Dex20-$R_5H_5$ (20%) and Dex70-$R_5H_5$ (10%), were obtained. These Dex-$R_5H_5$ hybrids polymers served as the nucleic acid "carrier" or "vector" in the Dex-$R_5R_5$/DNA and Dex-$R_5H_5$/microRNA149 antagomir complexes described and discussed below.

Particle size and surface charge are two important factors that influence transfection efficiency both in vitro and in vivo. Different Dex-R$_5$H$_5$/DNA complexes were formed at the N/P ratios from 1 to 30, and their size and surface charge were determined by dynamic light scattering (DLS). See Example 5. As shown in Table 1, the size of all Dex-R$_5$H$_5$/DNA complexes follows a similar trend, which increases at low N/P ratios and then decreases after that. The phenomenon has been observed in many similar systems. It has been found that the size of carrier/DNA complexes is controlled by two factors, the binding ability of carrier to DNA and the surface charge of complexes, but two factors cannot be completely separated. At low N/P ratios (1 and 5), the electrostatic interaction was not strong enough to form compact complexes due to low carrier concentration. At higher concentrations, more carrier molecules can condense DNA to form much smaller complexes. Also for particles with net surface charge, the repulsion force between particles prevents them from aggregating. During the transition between negative and positive, particles tend to aggregate due to weaker repulsion forces. In this system, the transitional point of particle surface charge appeared between N/P ratio 1 and 5. Among all tested N/P ratios of Dex-R$_5$H$_5$ vectors, small particles were achieved at the N/P ratio of 30. For the vector with Dex70, the particle size is 184 nm, which is much smaller than that of the vector system with Dex10 or Dex20. It indicates that dextran with high molecular weight (70 kDa) has better condensing ability than low molecular weight dextran (20 and 10 kDa).

TABLE 1

Hydrodynamic size and zeta potential of Dex10-R$_5$H$_5$(20%)/DNA, Dex10-R$_5$H$_5$(40%)/DNA, Dex20-R$_5$H$_5$(10%)/DNA, Dex20-R$_5$H$_5$(20%)/DNA and Dex70-R$_5$H$_5$(10%)/DNA complexes.

| Carrier | N/P | Size (d.nm) | SD (±d.nm) | Zeta (mV) | SD (±mV) |
|---|---|---|---|---|---|
| Dex10-R5H5 (20%) | 1 | 245 | 17 | −10.2 | 1.1 |
| | 5 | 377 | 10 | 5.2 | 0.6 |
| | 10 | 306 | 25 | 6.0 | 0.5 |
| | 20 | 304 | 24 | 6.5 | 0.1 |
| | 30 | 276 | 26 | 6.9 | 0.5 |
| Dex10-R5H5 (40%) | 1 | 86 | 4 | −15.2 | 0.1 |
| | 5 | 263 | 26 | 6.8 | 0.8 |
| | 10 | 345 | 33 | 5.7 | 0.2 |
| | 20 | 276 | 25 | 9.7 | 0.4 |
| | 30 | 256 | 25 | 10.9 | 0.3 |
| Dex20-R5H5 (10%) | 1 | 203 | 20 | −6.2 | 0.5 |
| | 5 | 426 | 31 | 0.3 | 0.7 |
| | 10 | 334 | 21 | 4.2 | 0.6 |
| | 20 | 307 | 21 | 5.3 | 0.7 |
| | 30 | 291 | 27 | 5.3 | 0.7 |
| Dex20-R5H5 (20%) | 1 | 102 | 18 | −13.7 | 0.4 |
| | 5 | 310 | 17 | 4.3 | 0.2 |
| | 10 | 295 | 22 | 8.7 | 0.7 |
| | 20 | 269 | 24 | 8.7 | 0.2 |
| | 30 | 268 | 23 | 9.3 | 0.6 |
| Dex70-R5H5 (10%) | 1 | 262 | 9 | −0.1 | 0.3 |
| | 5 | 287 | 27 | 2.0 | 0.6 |
| | 10 | 221 | 20 | 3.0 | 0.5 |
| | 20 | 199 | 9 | 2.9 | 0.6 |
| | 30 | 184 | 10 | 3.8 | 0.2 |

As can be seen from Table 1, the zeta potential of the Dex-R$_5$H$_5$/DNA complexes increased dramatically from the N/P ratio of 1 to 5 and did not change much above the N/P ratio of 5. The zeta potential of Dex70-R$_5$H$_5$/DNA complexes was lower than that of Dex20-R$_5$R$_5$/DNA or Dex10-R$_5$H$_5$/DNA complexes at the same N/P ratio. This phenomenon can be explained with the DS (10%) of R$_5$H$_5$ in Dex70-R$_5$H$_5$. For Dex20-R$_5$H$_5$ or Dex10-R$_5$H$_5$ with different DS (10%-40%), the zeta potential of Dex-R$_5$H$_5$/DNA complexes at high substitution degree was higher than that of complexes at low substitution degree. It was reported that net positive charge of carrier/nucleic acid complexes facilitates their cellular uptake because of the interaction of the negatively charged cell membrane and the positively charged complexes. However, if the charge density of the complexes is too high (>30 mV), it might induce cellular toxicity and reduce their blood circulation time and specificity to target cells due to the elevated nonspecific binding to serum protein and cells. The results show that Dex-R$_5$H$_5$ vesicles can efficiently condense DNA to the desired size and surface potential in vitro.

To evaluate the binding affinity of polysaccharide polymer compositions according to embodiments of the present invention to the nucleic acids being delivered (a critical factor for the delivery and release of the nucleic acids), the DNA binding ability of Dex-R$_5$H$_5$ vectors were evaluated by agarose electrophoresis for Dex-R$_5$H$_5$/DNA complexes formed at different N/P ratios (1 to 30). See Example 6. As shown in FIGS. 6A-E, Dex20-R$_5$H$_5$/DNA and Dex10-R$_5$H$_5$/DNA complexes formed at the N/P ratio of 1 traveled slightly shorter than the naked DNA across the gel, which indicates incomplete retardation of DNA at the N/P ratio of 1, and the complete retardation of DNA was achieved at the N/P ratio of 5. For Dex70-R$_5$H$_5$(10%), the complete retardation of DNA was achieved at even the N/P ratio of 1, which indicates that Dex70-R$_5$H$_5$ has better condensing ability than Dex10-R$_5$H$_5$ and Dex20-R$_5$H$_5$ hybrids. This result agrees with the result observed above in the section of size and zeta-potential of Dex-R$_5$H$_5$/DNA complexes.

To study whether use of the Dex-R$_5$H$_5$ hybrids of embodiments of the present invention as gene carriers can enhance the transgene expression in vitro, transfection efficiency of five Dex-R$_5$H$_5$ hybrids were evaluated in a model cancer cell line, SKOV-3. See Example 7. For all Dex10-R$_5$H$_5$ and Dex20-R$_5$H$_5$ hybrids, high luciferase expression levels (FIG. 7A) were achieved at the N/P ratio of 1, which are about three orders of magnitude greater than that of naked DNA. Besides, as N/P ratio increases from 1 to 30, the luciferase expression level increased first and then followed a decreasing trend. For the Dex10-R$_5$H$_5$ system, the highest expression level of Dex10-R$_5$H$_5$ (20%) was achieved at the N/P of 5 (9.4×10$^8$ RLU/mg protein). The Dex10-R$_5$H$_5$ (40%) induced 50% higher luciferase expression with a value of 7.3×10$^9$ RLU/mg protein than PEI/DNA at the same N/P ratio (5). The highest expression level of Dex10-R$_5$H$_5$ (40%) achieved at the N/P ratio of 20 and it is 90% higher than PEI/DNA. The highest expression levels of Dex20-R$_5$H$_5$ at 10% and 20% DS were both achieved at the N/P of 10, 3.0×10$^9$ and 3.5×10$^9$ RLU/mg protein, respectively, which are comparable to the luciferase expression (4.8×10$^9$ RLU/mg protein) induced by PEI/DNA at the N/P ratio of 5. FIG. 7B shows that the Dex70-R$_5$H$_5$(10%)/DNA complexes induced relatively lower luciferase expression than other Dex-R$_5$H$_5$/DNA complexes derived from low molecular weight dextran (20 and 10 kDa). The luciferase expression level of Dex70-R$_5$H$_5$ (10%)/DNA complexes increased slightly as the N/P ratio increases from 1 to 15, and the luciferase expression level achieved at the N/P of 15 was three orders of magnitude lower than that of PEI/DNA. While not to be bound by theory, it is believed that the low expression level of Dex70-R$_5$H$_5$ (10%)/DNA complexes could be caused by its stronger DNA condensing ability, which leads to inefficient unpacking and release of condensed DNA. (See Ramsay, E.; Hadgraft, J.; Birchall, J.; Gumbleton, M., Examination of the biophysical interaction between plasmid DNA and the polycations, polylysine and polyornithine, as a basis for their differential gene transfection in-vitro. *Int. J. Pharm.* 2000, 210, (1-2), 97-107, the disclosure of which is hereby incorporated by reference in its entirety). It has been found that Dex-$R_5H_5$ vector systems with low molecular weight dextran (10 and 20 kDa) have greater gene transfection efficiency than dextran with higher molecular weight.

While not to be bound by theory, it is believed that this increased efficiency may be attributed to three factors. First, the weaker DNA condensation of Dex10-$R_5H_5$ and Dex20-$R_5H_5$ hybrids could facilitate the disassembly of Dex-$R_5H_5$/DNA complexes in nuclei, which is critical for transcription of the luciferase gene carried by the plasmid DNA. Second, the higher zeta potential of Dex-$R_5H_5$/DNA complexes derived from low molecular weight dextran may lead to an increased interaction with cell surfaces and cellular uptake. Third, Dex10-$R_5H_5$ and Dex20-$R_5H_5$ may possess higher buffering capacity and subsequently lead to more effective lysosomal escape, because Dex10-$R_5H_5$ and Dex20-$R_5H_5$ with higher DS (10-40%) of $R_5H_5$ contains more imidazole groups compared to Dex70-$R_5R_5$ (10%). As discussed above, low molecular weight and high DS of $R_5H_5$ in Dex-$R_5H_5$ system are favorable for gene transfection.

Cytotoxicity of Dex-$R_5H_5$/DNA complexes was determined against SKOV-3 cells using MTT assay, and then compared with that of naked DNA as a negative control and PEI/DNA (N/P 5) as a positive control. See Example 9. The DNA concentration is 5 μg/mL for all samples. Dex10-$R_5H_5$/DNA and Dex20-$R_5H_5$/DNA complexes have higher cell viability (above 80%) at N/P ratios between 1 to 10 and generally follows a decreasing trend as N/P ratio increases from 1 to 30 (FIG. 8A). In particular, Dex10-$R_5H_5$ (40%)/DNA complexes induced the lowest cytotoxicity among the five Dex-$R_5H_5$ systems, and its cytotoxicity at all tested N/P ratios (1 to 30) were all lower than 25 kDa PEI at the N/P ratio of 5. At the N/P ratio of 5, Dex10-$R_5H_5$ (40%)/DNA complexes showed much higher cell viability (93%) than PEI/DNA complexes at the same N/P ratio. In contrast, as shown in FIG. 8B, Dex70-$R_5H_5$ (10%)/DNA complexes at a lower N/P range, from 1 to 15, all induced relatively low cell viability which is 60-70%. The results indicate that the Dex70 system is more toxic to cells than Dex10 and Dex20 systems. Similar results have been reported in other polycation systems, which an increase in cytotoxicity is as a function of the molecular weight. It should be noted that the cytotoxicity of all five Dex-$R_5H_5$ hybrids/DNA complexes at the N/P of 5 (below 20%) is lower than that (34%) of PEI (25 kDa)/DNA complex at the same N/P ratio. We expect that the Dex-$R_5H_5$ will have even lower in vivo toxicity than PEI. The further study is planned to investigate the in vivo transfection efficiency and cytotoxicity of Dex-$R_5H_5$ hybrids.

All Dex-$R_5H_5$ hybrids tested showed strong DNA binding ability at low N/P ratios. Dex-$R_5H_5$ hybrids derived from low molecular weight dextran (10 and 20 kDa) have greater gene transfection efficiency and lower cytotoxicity than that with high molecular weight dextran (70 kDa). The best performance on gene expression was achieved by Dex10-$R_5H_5$ at a 40% degree of substitution (DS), which induced greater gene expression than that of PEI/DNA at the N/P ratio of 5, and it also has much higher cell viability (93%) than that of PEI/DNA (66%). These results indicate that the hybrid Dex10-$R_5H_5$ at 40% DS may be a promising delivery system for safe and efficient gene therapy.

As set forth above, MicroRNAs (miRNAs) are non-coding RNAs that play critical roles in a broad range of biologic processes, including differentiation, proliferation, cell cycle regulation and apoptosis. MiRNA expression is commonly deregulated in almost all types of diseases, including cancers. MiRNAs aberrantly express during cancer development, invasion and metastasis, and function as either oncogenes or tumor suppressors. Thus, the use of miRNA machinery to regulate the dysregulated mRNA expression in diseases has drawn significant attention in biomedical research. The advantage of using miRNA-based cancer therapy over small interfering RNA (siRNA)/short hairpin RNA (shRNA) is the "one hit, multiple targets" effects[10]. MiRNA-based gene therapy provides a potential promising therapeutic approach for cancers and other gene related diseases in clinical applications.

Naked miRNAs are unstable and polyanionic, which reduces half-life and impedes efficient cellular uptake. Therefore, the success of miRNA therapy depends on effective delivery systems for microRNAs. RNA interference (RNAi)-based gene therapy has been in use for several years, and the systems developed for delivering siRNA/short hairpin RNA (shRNA) in preclinical models has been employed in miRNA delivery, through viral vectors, liposomes, and nanoparticles. While non-viral vectors, such as liposomes and nanoparticles, are not as efficient as viral vectors, they provide safer delivery strategies since they avoid the problems associated with viruses, including complexity of production, immunogenicity and mutagenesis. Unfortunately, however, while many of these known non-viral vectors have been shown to induce high gene transfection in vitro, however, these systems have also shown increased toxicity, low biodegradability and poor biocompatibility in vivo. The polymer compositions of embodiments of the present invention, however, achieve high transfection efficiency and low cytotoxicity at low vector/plasmid DNA ratios.

To evaluate the usefulness of the polymer compositions of embodiments of the present invention as a delivery carrier for microRNA drugs, MicroRNA149 antagomirs, a model drug of microRNAs, was complexed with Dex10-$R_5H_5$ (40%) at different N/P ratios. See Example 4, below. The size and zeta potential of the complexes, and microRNA binding ability were characterized by dynamic light scattering (DLS) and agarose gel electrophoresis, respectively. See Examples 5 and 6, below. To evaluate the utility of Dex10-$R_5H_5$ (40%) as an efficient and effective vector to deliver microRNAs, cellular uptake, gene expression and cytotoxicity were evaluated against human liver hepatocellular carcinoma HepG2 cells, in comparison with that of commercially available transfection reagent RNAiMAX. See Examples 8-10, below.

As set forth above, the size and surface charge of a drug carrier are two important factors that influence the delivery efficiency of its drug, microRNA, in vitro and in vivo. To study the effect of size and surface charge of carrier/drug nanoparticles on drug delivery efficiency, a model drug miRNA149 antagomir was condensed with cationic Dex10-$R_5H_5$ (40%) at various N/P ratios through electrostatic interactions. Here, the N/P ratio is a molar ratio of arginine residue (N) in the peptide to phosphate group (P) in the microRNA molecule. Both size and zeta-potential of Dex10-$R_5H_5$ (40%)/miRNA149 antagomir complexes were characterized by DLS. As shown in Table 2, the size of complexes decreased as the N/P ratio increased from 0.5 to 30. At the N/P ratio of 0.5, the amount of Dex10-$R_5H_5$ (40%) added into miRNA solution was not enough to cover its negative-charged surface and form condensed particles.

As more Dex10-$R_5H_5$ (40%) was added at the N/P ratio of 1, the size of Dex10-$R_5H_5$ (40%)/miRNA149 antagomir complexes dropped to 106 nm and the surface charge of the complexes increased from −10.0 mV to 1.0 mV. At N/P 2, the surface charge of the complexes increased to 15.0 mV and stayed similar above N/P 2, and a smaller size of the nanoparticles was achieved, indicating a condensed nanoparticle was formed. On the other hand, the net positive charge of carrier/nucleic acid complexes facilitates their cellular uptake because of the interaction of the negatively charged cell membrane and the positively charged complexes. However, if the charge density of the complexes is high (>30 mV), it might induce cellular toxicity, and reduce their blood circulation time and specificity to target cells due to the elevated nonspecific binding to serum protein and cells. The results showed that Dex10-$R_5H_5$ (40%) vesicle can efficiently condense miRNA antagomirs to the desired size and surface potential in vitro.

TABLE 2

Hydrodynamic size and zeta potential of Dex10-$R_5H_5$ (40%)/microRNA149 antagomir complexes.

| Complexes | N/P | Size (d.nm) | SD (±d.nm) | Zeta (mV) | SD (±mV) |
|---|---|---|---|---|---|
| Dex10-$R_5H_5$ (40%)/ miRNA149 antagomir | 0.5 | 198 | 19 | −10.0 | 0.6 |
| | 1 | 106 | 0 | 1.0 | 0.2 |
| | 2 | 69 | 3 | 15.0 | 1.5 |
| | 3 | 70 | 2 | 18.8 | 1.4 |
| | 4 | 49 | 2 | 14.4 | 2.9 |
| | 5 | 36 | 1 | 13.3 | 1.5 |
| | 10 | 50 | 2 | 15.6 | 0.5 |
| | 20 | 21 | 9 | 10.5 | 1.8 |
| | 30 | 13 | 14 | 17.6 | 6.9 |
| RNAiMAX/ miRNA149 antagomir | | 629 | 201 | −32 | 1 |
| Dex10-$R_5H_5$ (40%) | 0 | 3 | 2 | 3.4 | 1.7 |

To evaluate the binding affinity of Dex10-$R_5H_5$(40%) to miRNA antagomirs, Dex10-$R_5H_5$ (40%)/miRNA149 antagomir complexes formed at various N/P ratios, ranging from 0.5 to 20, were analyzed by agarose gel electrophoresis. As shown in FIG. 9, nearly all miRNA antagomirs that used for condensation run through the agarose gel at tested N/P ratios from 0.5 to 20, compared to naked miRNA antagomirs at the N/P ratio of 0. A similar phenomenon was observed from RNAiMAX/miRNA149 antagomir complexes. These results indicate that miRNA antagomirs complexed with either Dex10-$R_5H_5$ (40%) or RNAiMAX were easily pulled apart from the complexes under the electric force. The binding ability of Dex10-$R_5H_5$ (40%) to miRNA antagomirs is weaker under the electrical field. This may be explained by the much smaller size and single strand of miRNA149 antagomir (23 bases) compared to the plasmid drug (~5200 base pairs), which makes the complexes formed between miRNA antagomir and Dex10-$R_5H_5$ (40%) less compact than those formed between the plasmid drug and Dex-$R_5H_5$ vectors even at high N/P ratios.

In one set of experiments, human liver hepatocellular carcinoma cell line HepG2 was used as the model cell to evaluate the delivery efficiency of Dex-$R_5H_5$ for microRNA149 antagomir. See Example 10. The ability of Dex10-$R_5H_5$ (40%) as a vector to delivery miRNA149 antagomir to HepG2 cells was observed by confocal laser scanning microscopy (CLSM) (FIG. 10). After incubated with Dex10-$R_5H_5$ (40%)/miRNA149 antagomir complexes formed at N/P ratios of 1, 2 and 4 for 6 hours, nearly all the cells displayed red fluorescence in cytoplasmic space, indicating efficient delivery of miRNA149 antagomir by Dex10-$R_5H_5$ (40%) into cells can be achieved at N/P ratios of 1, 2 and 4. For cells treated with RNAiMAX/miRNA149 antagomir complexes, a much lower red fluorescence intensity was observed than that of cells treated with Dex-R5H5/miRNA149 antagomir complexes. Under the 40× objective lens, the significant difference in cellular uptake of Dex10-$R_5H_5$ (40%)/miRNA149 antagomir complexes and RNAiMAX/miRNA149 inhibitor complexes was confirmed. Besides, the morphology of the complexes formed by Dex-$R_5H_5$ and RNAiMAX respectively was different. The miRNA149 antagomir delivered by Dex-$R_5H_5$ was widely dispersed around the nucleus. In contrast, the miRNA149 antagomir delivered by RNAiMAX aggregated in the perinuclear region, indicating these complexes are likely to be trapped in endosomes/lysosomes. The results by CLSM indicated that miRNA149 antagomir delivered by Dex10-$R_5H_5$ (40%) could be efficiently internalized by cells (~100%) and disperse widely in cytoplasm instead of being trapped in endosomes/lysosomes for enzymatic degradation.

Since Dex10-$R_5H_5$ (40%)/miRNA149 antagomir complexes exhibited enhanced cellular uptake, cytosolic localization, and high loading density, we postulated that Dex10-$R_5H_5$ (40%) loaded with microRNA149 antagomir could effectively inhibit microRNA, specifically microRNA149. To determine the inhibition of microRNA149 by microRNA149 antagomir, the microRNA149 expression level in HepG2 cells was studied by quantitative reverse transcriptase-polymerase chain reaction (RT-PCR). As FIG. 11 shows, the miRNA149 expression levels in cells treated with Dex10-$R_5H_5$ (40%)/miRNA149 antagomir complexes at N/P ratios of 1, 2 and 4 decreased to 52%, 48% and 24%, respectively, compared to the expression levels in cells treated with Dex10-$R_5H_5$ (40%)/miRNA NC complexes. As the N/P ratio of Dex10-$R_5H_5$ (40%)/miRNA149 antagomir complexes increased, the inhibition of the microRNA149 expression level was enhanced. At the N/P ratio of 4, the inhibition of microRNA149 expression (24%) was even stronger than that induced by RNAiMAX/microRNA149 antagomir complexes (33%). The results indicated that Dex10-$R_5H_5$ (40%) loaded with microRNA149 inhibitor could effectively inhibit microRNA149 expression, and even achieved higher efficiency than the commercially available transfection reagent RNAiMAX.

Cytotoxicity of Dex10-$R_5R_5$(40%)/microRNA149 antagomir complexes was determined against HepG2 cells using MTT assay, and compared with RNAiMAX/microRNA149 antagomir complexes. See Example 9, below. The microRNA antagomir concentration is 50 pmol/mL for all samples. As shown in FIG. 12, the cells treated with Dex10-$R_5H_5$ (40%) loaded drugs, miRNA 149 antagomir or miRNA NC, had very high viability at N/P ratios of 1, 2 and 4, which was about 100% compared to control cells. The result indicated that Dex10-$R_5H_5$ (40%) as a drug carrier exhibited no cytotoxicity to HepG2 cells. In contrast, RNAiMAX/miRNA complexes induced significant cytotoxicity to HepG2 cells, 48% by RNAiMAX/miRNA149 antagomir and 39% by RNAiMAX/miRNA NC, compared to control cells. Considering the absence of in vitro cytotoxicity, we expect that the Dex10-R5H5(40%) will have minimal in vivo toxicity.

Overall, the size and zeta potential of Dex10-$R_5H_5$ (40%)/microRNA149 antagomir complexes exhibited preferable values for intravenous gene delivery. MiRNA149 antagomir delivered by Dex10-$R_5H_5$ (40%) can be efficiently internalized by cells (~100%) and disperse widely in cytoplasm instead of being trapped in endosomes/lysosomes where enzymatic degradation dominates. Dex10-$R_5H_5$ (40%) loaded with microRNA149 antagomir could effectively inhibit microRNA149 expression (24%), and even achieve higher inhibition efficiency than the commercially available transfection reagent RNAiMAX (33%), while exhibiting no cytotoxicity to HepG2 cells as a drug carrier. These results indicate that the hybrid Dex10-$R_5H_5$ at 40% DS is a promising delivery system for safe and efficient miRNA-based gene therapy.

In light of the foregoing, it should be appreciated that the present invention significantly advances the art by providing a dextran-peptide hybrid gene delivery system that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Dextran (Dex10, Mw 9-11 kDa), Dextran (Dex20, Mw 15-25 kDa), Dextran (Dex70, Mw 64-76 kDa), glycidyl methacrylate (GMA), 4-(Dimethylamino)pyridine (DMAP), dimethyl sulfoxide (DMSO), phosphate-buffered saline (PBS) and polyethylenimine (PEI, branched, Mw 25 kDa) were purchased from Sigma-Aldrich (St Louis, Mo., USA). Tris(2-carboxyethyl)phosphine hydrochloride (TCEP) was purchased from Chem-Impex International (Wood Dale, Ill., USA). The peptide, $NH_2$—RRRRRHHHHHC—COOH ($R_5H_5C$) was synthesized at >95% purity by GenScript (Piscataway, N.J., USA). Agarose, 3-(4,5-Dimethylthiazol-2-yl)-2,5-Diphenyltetrazolium Bromide (MTT), Dulbecco's Modified Eagle Medium (DMEM), fetal bovine serum (FBS), penicillin, streptomycin, non-essential amino acids, sodium pyruvate, GlutaMAX™ and Trypsin-EDTA Lipofectamine® RNAiMAX reagent, nuclease-free water, ProLong® Gold Antifade Reagent, mirVana™ miRNA isolation kit, TaqMan® microRNA reverse transcription kit, TaqMan® universal PCR master mix and Hoechst 433342 nucleic acid stain were all purchased from Life Technologies (Carlsbad, Calif., USA). Ethidium bromide and nuclease-free water were purchased from EMD Millipore (Billerica, Mass., USA). Tris/Borate/EDTA (TBE) was purchased from AMRESCO (Solon, Ohio, USA). DNA loading dye was purchased from New England Biolabs (Ipswich, Mass., USA). Glo lysis buffer and luciferase assay system were purchased from Promega (Madison, Wis., USA). BCA protein assay kit was purchased from Thermo Scientific (Waltham, Mass., USA). Plasmid DNA encoding a 5.2 kb firefly luciferase (pCMV-luc) was purchased from Elim Biopharmaceuticals (Hayward, Calif., USA). SKOV-3 cell line was purchased from ATCC (St. Cloud, Minn., USA) and cultured in DMEM medium supplemented with 10% fetal bovine serum, non-essential amino acids, sodium pyruvate, GlutaMAX™ and penicillin-streptomycin at 37° C. in a humidified atmosphere of 5% $CO_2$. Label IT® siRNA Tracker Intracellular Localization kit (TM-Rhodamine) was purchased from Mirus (MirusBio, Wis., USA). MicroRNA149 antagomir and negative control microRNA inhibitor were synthesized by Integrated DNA Technologies (Coralville, Iowa). The primers (Tagman® Assays) for microRNA-149, microRNA-NT and U6 snRNA were ordered from Life Technologies (Carlsbad, Calif., USA). HepG2 cell line was purchased from ATCC (St. Cloud, Minn., USA) and cultured in DMEM medium supplemented with 10% fetal bovine serum, non-essential amino acids, sodium pyruvate, GlutaMAX™ and penicillin-streptomycin at 37° C. in a humidified atmosphere of 5% $CO_2$.

Example 1

Synthesis of Methacrylate Functionalized Dextran (Dex-MA)

Methacrylate functionalized dextran (Dex-MA) was synthesized following a published procedure. See, vanDijk-Wolthuis, W. N. E.; KettenesvandenBosch, J. J.; vanderKerkvanHoof, A.; Hennink, W. E., Reaction of dextran with glycidyl methacrylate: An unexpected transesterification. *Macromolecules* 1997, 30, (11), 3411-3413 and/or Cao, B.; Li, L. L.; Wu, H. Y.; Qiong, T.; Sun, B. B.; Dong, H.; Zhe, J.; Cheng, G., Zwitteration of dextran: a facile route to integrate antifouling, switchability and optical transparency into natural polymers. *Chem. Commun.* 2014, DOI: 10.1039/c3cc48878k, the disclosures of which are hereby incorporated by reference in their entirety. 500 mg of dextran was dissolved in 8 mL of dimethyl sulfoxide (DMSO) in a stoppered 25 mL round bottom flask under nitrogen atmosphere. Then 450 mg of 4-(dimethylamino) pyridine (DMAP) was dissolved in DMSO, and a calculated amount of glycidyl methacrylate (GMA) was added. The solution was stirred for 4 days at room temperature, and then an equimolar amount of concentrated HCl was added to neutralize DMAP and thereby stopping the reaction. The reaction mixture was dialyzed against deionized (DI) water for 4 days at 4° C. The Dex-MA was then lyophilized into a white powder, and analyzed with $^1$H-NMR. See FIG. 1.

Example 2

Preparation Dextran-Peptide Conjugate

The conjugation of the Dex-MA of Example 1 and peptide $R_5H_5C$ was carried out in DI water, as follows. $R_5H_5C$ (25 mg) was dissolved in DI water (50 μL) and 200 mM Tris(2-carboxyethyl)phosphine hydrochloride (TCEP) (19.7 μL) was added to reduce disulfide bonds that may form between two peptides. The mixture was incubated at room temperature for 5 minutes, followed by the addition of 1M NaOH (25 μL) to neutralize TCEP and trifluoroacetic acid (TFA) from peptide synthesis. A calculated amount (weight) of Dex-MA was provided in a separate tube and an amount of DI water weighing three times the weight of Dex-MA was added, and sonicated for 5 minutes to allow Dex-$R_5H_5$ to be dissolved completely. The Dex-MA solution was then added into the peptide solution and 1M NaOH was used to adjust the final pH of the mixture to 8.0. The mixture was incubated at room temperature for 48 hours under gentle shaking to form a Dextran-$R_5H_5$ hybrid. The Dextran-$R_5H_5$ hybrid was purified with a Zeba Spin Desalting Column (Thermo Fisher Scientific Inc., Rockford, Ill., USA) and analyzed by $^1$H-NMR. See FIG. 1. The degree of substitution (DS) of $R_5H_5$, which is defined as the number of $R_5H_5$ peptide side chains per 100 dextran glucopyranose residues, was calculated by integration of the anomeric protons of dextran (5.0 ppm), and the integration of the protons from imidazole ring of histidine (6.9 and 7.7 ppm). See FIG. 1.

Example 3

Preparation of Dex-$R_5H_5$/DNA Complexes

The Dex-$R_5H_5$ hybrid of Example 2 was dissolved in water to make a stock solution at 10 mg/mL. The pCMV-luc plasmid DNA was prepared at a concentration of 1 mg/mL in nuclease-free water. The Dex-$R_5H_5$/DNA complexes were formed by mixing equal volume of Dex-$R_5H_5$ and DNA solutions at various N/P ratios, and then incubated at room temperature for 20 minutes to allow the complete electrostatic interaction between peptide and DNA molecules. The N/P ratio was calculated to be the molar ratio of arginine residues (N) in the peptide to phosphate groups (P) in the DNA molecule. The phosphate content of the DNA molecules was estimated based on the assumed 330 g/mol of the average molecular weight of the nucleotides, while the nitrogen content of the peptide molecule was estimated based on the number of arginine residues in each Dex-$R_5H_5$ hybrid.

Example 4

Preparation of Dex-$R_5H_5$/microRNA Complexes

The Dex-$R_5H_5$ hybrid of Example 2 was dissolved in sterile DI water to make a stock solution at 1 mg/mL. The microRNA was made in nuclease-free water at 100 µM by dilution. The Dex-$R_5H_5$/microRNA complexes were formed by mixing equal volume of Dex-$R_5H_5$ and microRNA solutions at various N/P ratios, and then incubating them for 20 minutes at room temperature to allow a complete electrostatic interaction between peptide and miRNA molecules. Here, the N/P ratio is a molar ratio of arginine residues (N) in the peptide to phosphate groups (P) in the microRNA molecule.

Example 5

Size and Zeta-Potential Measurements

Dex-$R_5H_5$/DNA complexes were prepared as described in Example 3 above at different N/P ratios. The size and zeta-potential of the Dex-$R_5H_5$/DNA complexes were measured by a Malvern Nano-ZS Zetasizer (UK). The size measurements were performed in disposable sizing cuvettes at a laser wavelength of 633 nm and a scattering angle of 173°, while the zeta-potential measurements were performed in disposable zeta-potential cells. Before the measurement, the Dex-$R_5H_5$/DNA complexes were diluted 10 times with PBS, and each measurement was repeated for 3 runs per sample at 25° C. The results are reported in Table 1 above.

Dex-$R_5H_5$/microRNA complexes were prepared as described in Example 4 above at different N/P ratios. The size and zeta-potential of the Dex-$R_5H_5$/microRNA complexes were determined by a Malvern Nano-ZS Zetasizer (UK). The size measurements were performed in disposable sizing cuvettes at a laser wavelength of 633 nm and a scattering angle of 173°, and the zeta-potential measurements were performed in disposable zeta-potential cells. Before each measurement, Dex-$R_5H_5$ complex solution was diluted 10 times with PBS. Each sample was measured for 3 times at 25° C. The results are reported in Table 2 above.

Example 6

Gel Retardation Assay

Dex-$R_5H_5$/DNA complex solutions were prepared at N/P ratios from 0 to 30. An aliquot (5 µL, 0.5 µg DNA) of each solution was mixed with loading dye and loaded to an agarose gel (0.8%). The loaded gel was exposed to 100 V for 40 min in 0.5×TBE buffer, and was stained in ethidium bromide (0.5 µg/mL) for 30 minutes and destained with water for 15 minutes. Then the gel was visualized and documented using a UVP BioDoc-It imaging system (Upland, Calif., USA). The results are reported in FIGS. 6A-E.

Dex-$R_5H_5$/microRNA complex solutions were prepared at N/P ratios from 0 to 10. An aliquot (20 pmol microRNA) of each solution was mixed with loading dye and loaded onto a 4% agarose gel. The loaded gel was exposed to 120 V for 40 min in 0.5×TBE buffer. Then the gel was stained in ethidium bromide (0.5 µg/mL) for 30 minutes and destained with water for 15 minutes. The gel was visualized and documented with a UVP BioDoc-It imaging system (Upland, Calif., USA). The results are reported in FIG. 9.

Example 7

In Vitro Gene Transfection and Expression

SKOV-3 cells were seeded at a density of 1×10$^5$ cells/mL onto a 24-well plate (0.5 mL/well) and incubated for 24 hours to reach 80-90% confluence. Then, old medium was replaced with 450 µL of fresh medium and 50 µL of the complex solution (containing 2.5 µg DNA) was added into each well. After 4 hours of incubation, the transfection medium was removed and replaced by 500 µL culture medium. Cells were incubated for another 68 hours. After incubation, cells were washed with PBS and 0.2 mL of 1×Glo lysis buffer was added to each well to lyse cells. After being incubated at room temperature for 15 minutes and subjected to two cycles of freezing (−80° C. for 30 minutes) and thawing (room temperature), cell lysates were centrifuged at 14,000 rpm at 4° C. for 15 minutes to remove cell debris. The supernatant (20 µL) was transferred to a luminometer tube and mixed with 100 µL of luciferase assay reagent, and the luciferase activity was immediately measured for a 10-second read by a Berthold Lumat LB9507 luminometer (Germany). The relative light unit (RLU) reading from the luminometer was normalized by the protein content in the supernatant, which was determined by BCA protein assay. All the experiments were performed with 4 replicates. The results are reported in FIGS. 7A, 7B.

Example 8

Intracellular Localization of Dex-$R_5H_5$/microRNA Complexes

Intracellular localization of Dex-$R_5H_5$/microRNA complexes in HepG2 cells was studied by an Olympus FLUOVIEW FV1000 confocal laser scanning microscopy (CLSM) (Japan). HepG2 cells were seeded on a Nalgene Lab-Tek™ II 8-well chamber slide (Waltham, Mass., USA) at a density of 20,000 cells/well and cultured for 24 hours. Then the medium was replaced by 180 µL of fresh medium, and 20 µL of the complex solutions containing 20 pmol Rhodamine-labeled microRNA was subsequently added into each well. The complex solution was Dex-$R_5H_5$ or RNAiMAX complexed with microRNA. Dex-$R_5H_5$/microRNA complexes were formed at the N/P ratios of 2 and 4, respectively, while RNAiMAX/microRNA complexes were formed according to manufacturer's instruction. Then the medium was removed and cells were washed with cold PBS three times after 6-hour incubation. 3.7% paraformaldehyde was applied to cells for 30 minutes to fix cells. Then the cells were washed with PBS three times again, and incubated in 100 µL of Hoechst 33342 at 2 µg/mL for 30 minutes. For microscopy imaging, the chamber slide was mounted with Prolong Gold Antifade solution and covered with a glass slip. The slide was then examined by CLSM with excitation at 405 and 559 nm for Hoechst 33342 and TM-Rhodamine, respectively, as well as differential interference contrast (DIC) microscopy.

The images were recorded and processed with Olympus FV10-ASW software. Under the 40× objective lens, the significant difference in cellular uptake of Dex10-$H_5H_5$ (40%)/miRNA149 antagomir complexes and RNAiMAX/miRNA149 inhibitor complexes was confirmed. Besides, the morphology of the complexes formed by Dex-$R_5H_5$ and RNAiMAX respectively was different. The miRNA149 antagomir delivered by Dex-$R_5H_5$ was widely dispersed around the nucleus. In contrast, the miRNA149 antagomir delivered by RNAiMAX aggregated in the perinuclear region, indicating these complexes are likely to be trapped in endosomes/lysosomes. The results by CLSM indicated that miRNA149 antagomir delivered by Dex10-$R_5H_5$ (40%) could be efficiently internalized by cells (~100%) and disperse widely in cytoplasm instead of being trapped in endosomes/lysosomes for enzymatic degradation See FIG. 10.

Example 9

Cytotoxicity Assay

The cytotoxicity of Dex-$R_5H_5$/DNA complexes was evaluated against SKOV-3 cell line in 96-well plate, following the procedure of Vybrant® MTT Cell Proliferation Assay (Life Technology, Carlsbad, Calif., USA). SKOV-3 cells were seeded on a 96-well plate and incubated for 24 hours. Then the old medium was replaced with 90 µL of fresh culture medium and 10 µL of the complex solution (0.5 µg DNA) was added to each well. The cells were incubated at 37° C. for 4 hours. Then the transfection medium was removed and replaced by 100 µL culture medium, and cells were incubated for another 20 hours. The medium was then replaced with 100 µL of the fresh medium and 10 µL of MTT stock solution (5 mg/mL in PBS), and cells were incubated at 37° C. for 4 hours. Finally, the medium was removed and 150 µL of DMSO was added to each well to dissolve purple formazan crystals. The absorbance of DMSO supernatant was measured at 540 nm using a Tecan Infinite 200 microplate reader (Switzerland). The cytotoxicity test was performed in 8 replicates of each sample. The cells treated with naked DNA were used as control, and the cell viability was expressed as a percentage of the control. The results are reported in FIGS. 8A, 8B.

The cytotoxicity of Dex-$R_5H_5$/microRNA complexes was evaluated against HepG2 cells using Vybrant® MTT Cell Proliferation Assay. Briefly, cells were seeding in 96 well-plates at the density of 20000 cells per well. After 24-hour incubation, the old medium was replaced with 90 µL of fresh medium and 10 µL of various formulations of drugs, including Dex-$R_5H_5$ with microRNA-149 or microRNA-NC at N/P ratios of 2 and 4. After incubation at 37° C. for 48 hours, the medium was replaced with 100 µL of fresh medium and 10 µL of MTT stock solution (5 mg/mL in PBS), and the cells were incubated for 4 hours at 37° C. Then, the medium was removed and 150 µL of DMSO was added to each well to dissolve the purple formazan crystals. The absorbance was measured at 570 nm using a Tecan Infinite 200 microplate reader (Switzerland). The cytotoxicity test was performed in 8 replicates for each sample. The cells without any treatment were used as a control (100% cell viability), and the cell viability was expressed as percentage of the control. The results are reported in FIG. 12.

Example 10

MicroRNA149 Quantification

The expression level of microRNA-149 in HepG2 cell line was analyzed by TaqMan MicroRNA Assay. Cells were plated (400,000 cells per well) on 6-well plates and cultured for 24 hours. Then old medium was replaced by 1.8 mL of fresh medium and 200 µL of various drug formulations, including Dex-$R_5H_5$ with microRNA149 or NC microRNA at N/P ratios of 2 and 4, and RNAiMAX with microRNA-149 or NC microRNA. After 48-hour incubation, total RNA was isolated using a mirVana™ miRNA isolation kit, followed by reversing transcribe RNA by a Taqman® Reverse Transcription kit with 10 ng of total RNA. Then TaqMan microRNA assay reaction mixture was prepared according to the provided protocol, and Real-time PCR amplification was carried out by a Bio-Rad CFX96 Real-Time Detection System (Hercules, Calif., USA). The PCR data was analyzed using qbase+ software (Belgium). The results are reported in FIG. 11.

Example 11

Synthesis of CB-Functionalized Dextran (CB-Dex)

4.9 mL (33.7 mmole) of N,N-dimethylglycine ethyl ester was dissolved and hydrolyzed in 15 mL of NaOH solution containing 1.35 g of NaOH (33.7 mmole) at 50° C. for overnight. After the removal of the byproduct (ethanol) with rotary evaporation, the solution was mixed with 1 g of dextran (70 k) (6.13 mmole of glucose unit) in water, followed by the addition of 2.5 mL of epichlorohydrin (30.6 mmole). The mixture was stirred at 55° C. for 2 days. After the reaction, the product was purified by cellulose dialysis membrane (14 k cut off) and lyophilized to obtain CB dextran (CB-Dex).

Example 12

Statistical Analysis

Gene transfection efficiency and cytotoxicity data analyzed using single-factor analysis of variance (ANOVA) and results were reported as mean±standard deviation from 4-8 replicates. Student's t-test was used for the comparison among groups. It was considered statistically significant, if the p value is less than 0.05.

What is claimed is:

1. A polysaccharide polymer composition for nucleic acid delivery comprising:
a polysaccharide polymer chain; and
one or more nucleic acid delivery side chains bonded to said polysaccharide polymer chain, wherein said one or more nucleic acid delivery side chains further comprise a cysteine-containing cationic peptide, and
one or more nucleic acids physically bonded to said cysteine-containing cationic peptide to form a polysaccharide-nucleic acid complex,
wherein the polysaccharide-nucleic acid complex has a molar ratio of amine or guanidine groups on the cysteine-containing cationic peptide of the nucleic acid delivery side chains (N) to the phosphate groups in the one or more nucleic acids (P) of from about 1:1 to about 20:1.

2. The polysaccharide polymer composition of claim 1 wherein said polysaccharide polymer chain comprises dextran, cellulose, starch, glycosaminoglycans, mannan, dextrin, agar, agarose, alginic acid, alguronic acid, amylose, alpha glucan, amylopectin, beta-glucan, callose, carrageenan, cellodextrin, chitin, chitosan, chrysolaminarin, cyclodextrin, DEAE-sepharose, ficoll, fructan, fucoidan, galactoglucomannan, galactomannan, gellan gum, glucan, glucomannan, glucuronoxylan, glycocalyx, glycogen, hemicellulose, homopolysaccharide, hypromellose, inulin, laminarin, lentinan, levan polysaccharide, lichenin, mixed-linkage glucan, paramylon, pectic acid, pectin, pentastarch, phytoglycogen, pleuran, polydextrose, polysaccharide peptide, porphyran, pullulan, sepharose, xylan, xyloglucan, zymosan, hyaluronan, heparin or combinations thereof.

3. The polysaccharide polymer composition of claim 1 wherein said polysaccharide polymer chain has a weight average molecular weight of from about 500 daltons to about 1,000,000 daltons.

4. The polysaccharide polymer composition of claim 1 wherein said one or more nucleic acid delivery side chains further comprise methacrylate, acrylate, methacrylamide, acrylamide, maleimide, haloacetyl, pyridyl disulfide, thiol or combinations thereof.

5. The polysaccharide polymer composition of claim 1 wherein the cationic peptide on each of said one or more nucleic acid delivery side chains is a random copolymer having a formula selected from the group consisting of $C_wR_5$, $C_wR_3H_3$, $C_wK_5$, $C_wK_3$, $C_wR_5H_5$, $C_wR_3H_3$, $C_wK_5H_5$, $C_wK_3H_3$, $C_wR_m$, $C_wK_n$, $C_wR_oH_p$, $C_wK_pH_q$, and $C_wR_xK_yH_z$; wherein C is cysteine, R is arginine, K is lysine, H is histidine, and m, n, o, p, q, x, y, z and w are integers from 1 to 1,000.

6. The polysaccharide polymer composition of claim 1 wherein the cationic peptide on each of said one or more nucleic acid delivery side chains is a block copolymer having a formula selected from the group consisting of $CR_5$, $CR_3H_3$, $CH_3R_3$, $CK_5$, $CK_3$, $CH_5R_5$, $CR_5H_5$, $CR_3H_3$, $CH_3R_3$, $CK_5H_5$, $CH_5K_5$, $CK_3H_3$, $CH_3K_3$, $R_5C$, $R_3H_3C$, $K_5C$, $K_3C$, $R_5H_5C$, $R_3H_3C$, $K_5H_5C$, $K_3H_3C$, $CR_m$, $CK_n$, $CR_oH_p$, $CK_pH_q$, $R_3H_7C$, $R_3H_5C$, $R_2H_6C$, $R_4H_6C$, $R_3H_8C$ and $CR_xK_yH_z$; wherein C is cysteine, R is arginine, K is lysine, H is histidine, and m, n, o, p, q, x, y, and z are integers from 1 to 1,000.

7. The polysaccharide polymer composition of claim 1 wherein said cationic peptide comprises from about 1 to about 10000 arginine residues, from about 1 to about 10000 histidine residues and at least one cysteine residue.

8. The polysaccharide polymer composition of claim 1 wherein said cationic peptide comprises from about 1 to about 10000 lysine residues, from about 1 to about 10000 histidine residues and at least one cysteine residue.

9. The polysaccharide polymer composition of claim 1 wherein said cationic peptide has the formula $NH_2$-RRRRRHHHHHC-COOH ($R_5H_5C$) (SEQ ID NO. 5).

10. The polysaccharide polymer composition of claim 1 wherein said one or more nucleic acid delivery side chains further comprise a linker molecule bound to said polysaccharide polymer chain; wherein said cationic peptide is bonded to said linker molecule by a thiol bond.

11. The polysaccharide polymer composition of claim 1, wherein the polysaccharide-nucleic acid complex has a molar ratio of amine or guanidine groups on the side chain of peptide (N) to the phosphate group in the nucleic acid (P) of from about 1:1 to about 10:1.

12. The polysaccharide polymer composition of claim 1 wherein said one or more nucleic acids comprise ribonucleic acids, deoxyribonucleic acids or combinations thereof.

13. The polysaccharide polymer composition of claim 1 wherein said one or more nucleic acids are selected from the group consisting of Plasmid DNA, Oligonucleotides, Aptamers, DNAzymes, RNA Aptamers, RNA Decoys, Antisense RNA, Ribozymes, small interfering RNA (siRNA), microRNA (miRNA), short hairpin RNA, Antagomirs, and combinations thereof.

14. The polysaccharide polymer composition of claim 1, further comprising one or more zwitterionic side chains.

15. The polysaccharide polymer composition of claim 14, wherein said one or more zwitterionic side chains comprise a zwitterionic moiety, said zwitterionic moiety comprising a carboxybetaine group, a sulfobetaine group, a phosphobetaine group or any combinations thereof.

16. The polysaccharide polymer composition of claim 14, wherein said zwitterionic moiety has a corresponding cationic ring form.

17. The polysaccharide polymer composition of claim 1 or 14 further comprising one or more reactive side chains comprising a compound selected from the group consisting of acrylates, methacrylates, methacrylamides, acrylamides, maleimides, haloacetyls, pyridyl disulfides, thiols and combinations thereof.

18. The polysaccharide polymer composition of claim 1, wherein the polysaccharide-nucleic acid complex has a molar ratio of amine or guanidine groups on the side chain of peptide (N) to the phosphate group in the nucleic acid (P) of from about 2:1 to about 10:1.

* * * * *